(12) United States Patent
Measamer et al.

(10) Patent No.: US 8,066,167 B2
(45) Date of Patent: Nov. 29, 2011

(54) CIRCULAR SURGICAL STAPLING INSTRUMENT WITH ANVIL LOCKING SYSTEM

(75) Inventors: John P. Measamer, Cincinnati, OH (US); Mark Tsonton, Loveland, OH (US); Nicholas G. Molitor, Milford, OH (US); Barry T. Jamison, Fairfield, OH (US); Scott B. Killinger, Loveland, OH (US); Randall S. Koplin, Fitchburg, WI (US); Wai N. Chin, Glenview, IL (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 211 days.

(21) Appl. No.: 12/408,905

(22) Filed: Mar. 23, 2009

(65) Prior Publication Data
US 2010/0237132 A1    Sep. 23, 2010

(51) Int. Cl.
*A61B 17/068* (2006.01)
(52) U.S. Cl. ............... 227/175.2; 227/179.1; 227/182.1
(58) Field of Classification Search ............. 227/19, 227/175.2, 175.3, 179.1, 182.1
See application file for complete search history.

(56) References Cited

U.S. PATENT DOCUMENTS

| | | | |
|---|---|---|---|
| 3,080,564 A * | 3/1963 | Strekopitov et al. ......... 227/153 |
| 3,490,675 A | 1/1970 | Green et al. |
| 3,643,851 A | 2/1972 | Green et al. |
| 3,662,939 A | 5/1972 | Bryan |
| 3,717,294 A | 2/1973 | Green |
| 3,819,100 A | 6/1974 | Noiles et al. |
| 4,304,236 A * | 12/1981 | Conta et al. ............... 227/179.1 |
| 4,331,277 A | 5/1982 | Green |
| 4,383,634 A | 5/1983 | Green |
| 4,396,139 A | 8/1983 | Hall et al. |
| 4,402,445 A | 9/1983 | Green |
| 4,415,112 A | 11/1983 | Green |
| 4,475,679 A | 10/1984 | Fleury, Jr. |
| 4,489,875 A | 12/1984 | Crawford et al. |
| 4,500,024 A | 2/1985 | DiGiovanni et al. |
| 4,505,414 A | 3/1985 | Filipi |
| 4,522,327 A | 6/1985 | Korthoff et al. |

(Continued)

FOREIGN PATENT DOCUMENTS
CA    2458946 A1    3/2003
(Continued)

OTHER PUBLICATIONS

Disclosed Anonymously, "Motor-Driven Surgical Stapler Improvements," Research Disclosure Database No. 526041, Published: Feb. 2008.

(Continued)

*Primary Examiner* — Rinaldi Rada
*Assistant Examiner* — Gloria R Weeks

(57) ABSTRACT

Circular stapling instruments for cutting and applying one or more surgical staples to tissue are disclosed. The instruments include various forms of anvil locking systems designed to selectively prevent the anvil from moving axially relative to the stapling head of the stapling instrument. One embodiment employs an elongated gear rack that is selectively engagable with locking gears to prevent axial motion of the elongated gear rack and an adjustment shaft used to axially position the anvil. Other embodiments employ a gear assembly that cooperates with the elongated gear rack. A locking member is movably supported by a handle assembly that houses the gear assembly and elongated gear rack. The locking member is configured for selective meshing engagement with the gear assembly to ultimately prevent axial movement of the gear rack and adjustment shaft.

14 Claims, 10 Drawing Sheets

U.S. PATENT DOCUMENTS

| | | | |
|---|---|---|---|
| 4,530,453 A | 7/1985 | Green | |
| 4,566,620 A | 1/1986 | Green et al. | |
| 4,573,622 A | 3/1986 | Green et al. | |
| 4,580,712 A | 4/1986 | Green | |
| 4,610,383 A | 9/1986 | Rothfuss et al. | |
| 4,629,107 A | 12/1986 | Fedotov et al. | |
| 4,664,305 A | 5/1987 | Blake, III et al. | |
| 4,671,445 A | 6/1987 | Barker et al. | |
| 4,715,520 A | 12/1987 | Roehr, Jr. et al. | |
| 4,728,020 A | 3/1988 | Green et al. | |
| 4,752,024 A | 6/1988 | Green et al. | |
| 4,754,909 A | 7/1988 | Barker et al. | |
| 4,767,044 A | 8/1988 | Green | |
| 4,805,823 A | 2/1989 | Rothfuss | |
| 4,817,847 A | 4/1989 | Redtenbacher et al. | |
| 4,819,853 A | 4/1989 | Green | |
| 4,821,939 A | 4/1989 | Green | |
| 4,869,414 A * | 9/1989 | Green et al. | 227/19 |
| 4,869,415 A | 9/1989 | Fox | |
| 4,941,623 A | 7/1990 | Pruitt | |
| 4,944,443 A | 7/1990 | Oddsen et al. | |
| 5,065,929 A | 11/1991 | Schulze et al. | |
| 5,104,025 A | 4/1992 | Main et al. | |
| 5,129,570 A | 7/1992 | Schulze et al. | |
| 5,137,198 A | 8/1992 | Nobis et al. | |
| 5,205,459 A | 4/1993 | Brinkerhoff et al. | |
| 5,221,036 A | 6/1993 | Takase | |
| 5,271,543 A * | 12/1993 | Grant et al. | 227/179.1 |
| 5,275,322 A * | 1/1994 | Brinkerhoff et al. | 227/175.1 |
| 5,285,945 A | 2/1994 | Brinkerhoff et al. | |
| 5,309,927 A | 5/1994 | Welch | |
| 5,518,163 A * | 5/1996 | Hooven | 227/5 |
| 5,535,935 A | 7/1996 | Vidal et al. | |
| 5,535,937 A | 7/1996 | Boiarski et al. | |
| 5,547,117 A | 8/1996 | Hamblin et al. | |
| 5,562,239 A | 10/1996 | Boiarski et al. | |
| 5,579,978 A | 12/1996 | Green et al. | |
| 5,584,425 A | 12/1996 | Savage et al. | |
| 5,597,107 A | 1/1997 | Knodel et al. | |
| 5,605,272 A | 2/1997 | Witt et al. | |
| 5,609,285 A * | 3/1997 | Grant et al. | 227/179.1 |
| 5,632,433 A | 5/1997 | Grant et al. | |
| 5,636,779 A | 6/1997 | Palmer | |
| 5,645,209 A | 7/1997 | Green et al. | |
| 5,647,526 A | 7/1997 | Green et al. | |
| 5,680,983 A | 10/1997 | Plyley et al. | |
| 5,685,474 A | 11/1997 | Seeber | |
| 5,706,997 A | 1/1998 | Green et al. | |
| 5,706,998 A | 1/1998 | Plyley et al. | |
| 5,709,334 A | 1/1998 | Sorrentino et al. | |
| 5,713,505 A | 2/1998 | Huitema | |
| 5,718,359 A | 2/1998 | Palmer et al. | |
| 5,718,360 A | 2/1998 | Green et al. | |
| 5,762,255 A | 6/1998 | Chrisman et al. | |
| 5,782,396 A | 7/1998 | Mastri et al. | |
| 5,794,834 A | 8/1998 | Hamblin et al. | |
| 5,799,857 A | 9/1998 | Robertson et al. | |
| 5,878,937 A | 3/1999 | Green et al. | |
| 5,893,506 A | 4/1999 | Powell | |
| 5,894,979 A | 4/1999 | Powell | |
| 5,915,616 A | 6/1999 | Viola et al. | |
| 5,918,791 A | 7/1999 | Sorrentino et al. | |
| 6,050,472 A * | 4/2000 | Shibata | 227/175.2 |
| 6,079,606 A | 6/2000 | Milliman et al. | |
| 6,109,500 A | 8/2000 | Alli et al. | |
| 6,155,473 A | 12/2000 | Tompkins et al. | |
| 6,193,129 B1 | 2/2001 | Bittner et al. | |
| 6,669,073 B2 | 12/2003 | Milliman et al. | |
| 6,959,852 B2 | 11/2005 | Shelton, IV et al. | |
| 6,988,649 B2 | 1/2006 | Shelton, IV et al. | |
| 7,059,508 B2 | 6/2006 | Shelton, IV et al. | |
| 7,097,089 B2 | 8/2006 | Marczyk | |
| 7,143,923 B2 | 12/2006 | Shelton, IV et al. | |
| 7,143,924 B2 | 12/2006 | Scirica et al. | |
| 7,143,925 B2 | 12/2006 | Shelton, IV et al. | |
| 7,172,104 B2 | 2/2007 | Scirica et al. | |
| 7,234,624 B2 | 6/2007 | Gresham et al. | |
| 7,303,108 B2 | 12/2007 | Shelton, IV | |
| 7,328,828 B2 | 2/2008 | Ortiz et al. | |
| 7,354,447 B2 | 4/2008 | Shelton, IV et al. | |
| 7,407,078 B2 | 8/2008 | Shelton, IV et al. | |
| 7,416,101 B2 | 8/2008 | Shelton, IV et al. | |
| 7,422,139 B2 | 9/2008 | Shelton, IV et al. | |
| 7,431,189 B2 | 10/2008 | Shelton, IV et al. | |
| 7,434,715 B2 | 10/2008 | Shelton, IV et al. | |
| 7,434,717 B2 | 10/2008 | Shelton, IV et al. | |
| 7,438,209 B1 | 10/2008 | Hess et al. | |
| 7,441,684 B2 | 10/2008 | Shelton, IV et al. | |
| 7,441,685 B1 | 10/2008 | Boudreaux | |
| 7,448,525 B2 | 11/2008 | Shelton, IV et al. | |
| 7,461,767 B2 | 12/2008 | Viola et al. | |
| 7,464,846 B2 | 12/2008 | Shelton, IV et al. | |
| 7,464,847 B2 | 12/2008 | Viola et al. | |
| 7,464,849 B2 | 12/2008 | Shelton, IV et al. | |
| 7,467,740 B2 | 12/2008 | Shelton, IV et al. | |
| 7,472,814 B2 | 1/2009 | Mastri et al. | |
| 7,472,815 B2 | 1/2009 | Shelton, IV et al. | |
| 7,490,749 B2 | 2/2009 | Schall et al. | |
| 7,500,979 B2 | 3/2009 | Hueil et al. | |
| 7,506,791 B2 | 3/2009 | Omaits et al. | |
| 7,510,107 B2 | 3/2009 | Timm et al. | |
| 7,556,186 B2 | 7/2009 | Milliman | |
| 7,588,175 B2 * | 9/2009 | Timm et al. | 227/179.1 |
| 7,644,848 B2 * | 1/2010 | Swayze et al. | 227/2 |
| 7,721,936 B2 * | 5/2010 | Shalton et al. | 227/180.1 |
| 7,766,209 B2 | 8/2010 | Baxter, III et al. | |
| 7,793,812 B2 | 9/2010 | Moore et al. | |
| 7,810,692 B2 | 10/2010 | Hall et al. | |
| 7,819,296 B2 | 10/2010 | Hueil et al. | |
| 7,819,297 B2 | 10/2010 | Doll et al. | |
| 7,819,298 B2 | 10/2010 | Hall et al. | |
| 7,832,612 B2 | 11/2010 | Baxter, III et al. | |
| 7,837,080 B2 | 11/2010 | Schwemberger | |
| 7,845,534 B2 | 12/2010 | Viola et al. | |
| 7,857,185 B2 | 12/2010 | Swayze et al. | |
| 7,857,186 B2 | 12/2010 | Baxter, III et al. | |
| 7,861,906 B2 | 1/2011 | Doll et al. | |
| 7,866,527 B2 | 1/2011 | Hall et al. | |
| 7,870,989 B2 | 1/2011 | Viola et al. | |
| 7,905,381 B2 | 3/2011 | Baxter, III et al. | |
| 2006/0060630 A1 | 3/2006 | Shelton, IV et al. | |
| 2006/0108393 A1 | 5/2006 | Heinrich et al. | |
| 2007/0034668 A1 | 2/2007 | Holsten et al. | |
| 2007/0045379 A1 | 3/2007 | Shelton, IV | |
| 2007/0102452 A1 | 5/2007 | Shelton, IV et al. | |
| 2007/0102453 A1 | 5/2007 | Morgan et al. | |
| 2007/0102472 A1 | 5/2007 | Shelton, IV | |
| 2007/0102473 A1 | 5/2007 | Shelton, IV et al. | |
| 2007/0102474 A1 | 5/2007 | Shelton, IV et al. | |
| 2007/0106317 A1 | 5/2007 | Shelton, IV et al. | |
| 2007/0158385 A1 | 7/2007 | Hueil et al. | |
| 2007/0170225 A1 | 7/2007 | Shelton, IV et al. | |
| 2007/0175949 A1 | 8/2007 | Shelton, IV et al. | |
| 2007/0175950 A1 | 8/2007 | Shelton, IV et al. | |
| 2007/0175951 A1 | 8/2007 | Shelton, IV et al. | |
| 2007/0175953 A1 | 8/2007 | Shelton, IV et al. | |
| 2007/0175955 A1 | 8/2007 | Shelton, IV et al. | |
| 2007/0175956 A1 | 8/2007 | Swayze et al. | |
| 2007/0175957 A1 | 8/2007 | Shelton, IV et al. | |
| 2007/0175958 A1 | 8/2007 | Shelton, IV et al. | |
| 2007/0175959 A1 | 8/2007 | Shelton, IV et al. | |
| 2007/0175964 A1 | 8/2007 | Shelton, IV et al. | |
| 2007/0179476 A1 | 8/2007 | Shelton, IV et al. | |
| 2007/0181632 A1 | 8/2007 | Milliman | |
| 2007/0194079 A1 | 8/2007 | Hueil et al. | |
| 2007/0194080 A1 | 8/2007 | Swayze et al. | |
| 2007/0194081 A1 | 8/2007 | Hueil et al. | |
| 2007/0194082 A1 | 8/2007 | Morgan et al. | |
| 2007/0225562 A1 | 9/2007 | Spivey et al. | |
| 2007/0233053 A1 | 10/2007 | Shelton, IV et al. | |
| 2007/0295780 A1 | 12/2007 | Shelton et al. | |
| 2008/0029570 A1 | 2/2008 | Shelton et al. | |
| 2008/0029573 A1 | 2/2008 | Shelton et al. | |
| 2008/0029574 A1 | 2/2008 | Shelton et al. | |
| 2008/0029575 A1 | 2/2008 | Shelton et al. | |
| 2008/0029576 A1 | 2/2008 | Shelton et al. | |
| 2008/0078800 A1 | 4/2008 | Hess et al. | |

| | | |
|---|---|---|
| 2008/0078801 A1 | 4/2008 | Shelton et al. |
| 2008/0078802 A1 | 4/2008 | Hess et al. |
| 2008/0078803 A1 | 4/2008 | Shelton et al. |
| 2008/0078804 A1 | 4/2008 | Shelton et al. |
| 2008/0078806 A1 | 4/2008 | Omaits et al. |
| 2008/0078807 A1 | 4/2008 | Hess et al. |
| 2008/0078808 A1 | 4/2008 | Hess et al. |
| 2008/0082115 A1 | 4/2008 | Morgan et al. |
| 2008/0082124 A1 | 4/2008 | Hess et al. |
| 2008/0082125 A1 | 4/2008 | Murray et al. |
| 2008/0082126 A1 | 4/2008 | Murray et al. |
| 2008/0164296 A1 | 7/2008 | Shelton et al. |
| 2008/0167522 A1 | 7/2008 | Giordano et al. |
| 2008/0167644 A1 | 7/2008 | Shelton et al. |
| 2008/0167670 A1 | 7/2008 | Shelton et al. |
| 2008/0167671 A1 | 7/2008 | Giordano et al. |
| 2008/0167672 A1 | 7/2008 | Giordano et al. |
| 2008/0167736 A1 | 7/2008 | Swayze et al. |
| 2008/0169328 A1 | 7/2008 | Shelton |
| 2008/0169329 A1 | 7/2008 | Shelton et al. |
| 2008/0169330 A1 | 7/2008 | Shelton et al. |
| 2008/0169331 A1 | 7/2008 | Shelton et al. |
| 2008/0169332 A1 | 7/2008 | Shelton et al. |
| 2008/0169333 A1 | 7/2008 | Shelton et al. |
| 2008/0210738 A1 | 9/2008 | Shelton et al. |
| 2008/0237296 A1 | 10/2008 | Boudreaux et al. |
| 2008/0296343 A1 | 12/2008 | Schall et al. |
| 2008/0296345 A1 | 12/2008 | Shelton, IV et al. |
| 2008/0296346 A1 | 12/2008 | Shelton, IV et al. |
| 2008/0296347 A1 | 12/2008 | Shelton, IV et al. |
| 2008/0300579 A1 | 12/2008 | Broehl et al. |
| 2008/0300580 A1 | 12/2008 | Shelton, IV et al. |
| 2008/0300613 A1 | 12/2008 | Shelton, IV et al. |
| 2008/0308601 A1 | 12/2008 | Timm et al. |
| 2008/0308602 A1 | 12/2008 | Timm et al. |
| 2008/0308603 A1 | 12/2008 | Shelton, IV. et al. |
| 2008/0308606 A1 | 12/2008 | Timm et al. |
| 2008/0308607 A1 | 12/2008 | Timm et al. |
| 2008/0314954 A1 | 12/2008 | Boudreaux |
| 2008/0314955 A1 | 12/2008 | Boudreaux et al. |
| 2008/0314956 A1 | 12/2008 | Boudreaux |
| 2008/0314957 A1 | 12/2008 | Boudreaux |
| 2008/0314961 A1 | 12/2008 | Boudreaux et al. |
| 2008/0314962 A1 | 12/2008 | Boudreaux |
| 2009/0001121 A1 | 1/2009 | Hess et al. |
| 2009/0001123 A1 | 1/2009 | Morgan et al. |
| 2009/0001124 A1 | 1/2009 | Hess et al. |
| 2009/0001125 A1 | 1/2009 | Hess et al. |
| 2009/0001126 A1 | 1/2009 | Hess et al. |
| 2009/0001128 A1 | 1/2009 | Weisenburgh, II et al. |
| 2009/0001130 A1 | 1/2009 | Hess et al. |
| 2009/0005807 A1 | 1/2009 | Hess et al. |
| 2009/0005808 A1 | 1/2009 | Hess et al. |
| 2009/0005809 A1 | 1/2009 | Hess et al. |
| 2009/0012556 A1 | 1/2009 | Boudreaux et al. |
| 2009/0057369 A1 * | 3/2009 | Smith et al. ............... 227/175.1 |
| 2009/0076534 A1 | 3/2009 | Shelton, IV et al. |
| 2009/0090763 A1 | 4/2009 | Zemlok et al. |
| 2009/0149871 A9 | 6/2009 | Kagan et al. |
| 2009/0206125 A1 | 8/2009 | Huitema et al. |
| 2009/0206126 A1 | 8/2009 | Huitema et al. |
| 2009/0206131 A1 | 8/2009 | Weisenburgh, II et al. |
| 2009/0206132 A1 * | 8/2009 | Hueil et al. ............... 227/175.2 |
| 2009/0206133 A1 | 8/2009 | Morgan et al. |
| 2009/0206137 A1 | 8/2009 | Hall et al. |
| 2009/0206138 A1 | 8/2009 | Smith et al. |
| 2009/0206139 A1 | 8/2009 | Hall et al. |
| 2009/0206140 A1 | 8/2009 | Scheib et al. |
| 2009/0206141 A1 | 8/2009 | Huitema et al. |
| 2009/0206142 A1 | 8/2009 | Huitema et al. |
| 2009/0206143 A1 | 8/2009 | Huitema et al. |
| 2009/0206144 A1 | 8/2009 | Doll et al. |
| 2009/0209946 A1 | 8/2009 | Swayze et al. |
| 2009/0209990 A1 | 8/2009 | Yates et al. |
| 2009/0242610 A1 | 10/2009 | Shelton, IV et al. |
| 2009/0289096 A1 | 11/2009 | Shelton, IV et al. |
| 2010/0032470 A1 | 2/2010 | Hess et al. |
| 2010/0065605 A1 | 3/2010 | Shelton, IV et al. |
| 2010/0069942 A1 | 3/2010 | Shelton, IV |
| 2010/0072252 A1 | 3/2010 | Baxter, III et al. |
| 2010/0076474 A1 | 3/2010 | Yates et al. |
| 2010/0076475 A1 | 3/2010 | Yates et al. |
| 2010/0089970 A1 | 4/2010 | Smith et al. |
| 2010/0089974 A1 | 4/2010 | Shelton, IV |
| 2010/0096435 A1 | 4/2010 | Fuchs et al. |
| 2010/0108741 A1 | 5/2010 | Hessler et al. |
| 2010/0127042 A1 | 5/2010 | Shelton, IV |
| 2010/0133317 A1 | 6/2010 | Shelton, IV et al. |
| 2010/0133318 A1 | 6/2010 | Boudreaux |
| 2010/0179382 A1 | 7/2010 | Shelton, IV et al. |
| 2010/0181364 A1 | 7/2010 | Shelton, IV et al. |
| 2010/0193566 A1 | 8/2010 | Scheib et al. |
| 2010/0193567 A1 | 8/2010 | Scheib et al. |
| 2010/0193568 A1 | 8/2010 | Scheib et al. |
| 2010/0193569 A1 | 8/2010 | Yates et al. |
| 2010/0198220 A1 | 8/2010 | Boudreaux et al. |
| 2010/0213241 A1 | 8/2010 | Bedi et al. |
| 2010/0222901 A1 | 9/2010 | Swayze et al. |
| 2010/0224669 A1 | 9/2010 | Shelton, IV et al. |
| 2010/0243709 A1 | 9/2010 | Hess et al. |
| 2010/0264193 A1 | 10/2010 | Huang et al. |
| 2010/0264194 A1 | 10/2010 | Huang et al. |
| 2010/0294829 A1 | 11/2010 | Giordano et al. |
| 2010/0301095 A1 | 12/2010 | Shelton, IV et al. |
| 2010/0301096 A1 | 12/2010 | Moore et al. |
| 2010/0305552 A1 | 12/2010 | Shelton, IV et al. |
| 2010/0308100 A1 | 12/2010 | Boudreaux |
| 2011/0006099 A1 | 1/2011 | Hall et al. |
| 2011/0006101 A1 | 1/2011 | Hall et al. |
| 2011/0006103 A1 | 1/2011 | Laurent et al. |
| 2011/0011914 A1 | 1/2011 | Baxter, III et al. |
| 2011/0011915 A1 | 1/2011 | Shelton, IV |
| 2011/0024477 A1 | 2/2011 | Hall et al. |
| 2011/0024478 A1 | 2/2011 | Shelton, IV |
| 2011/0024479 A1 | 2/2011 | Swensgard et al. |
| 2011/0042441 A1 | 2/2011 | Shelton, IV et al. |
| 2011/0060363 A1 | 3/2011 | Hess et al. |
| 2011/0062212 A1 | 3/2011 | Shelton, IV et al. |
| 2011/0068145 A1 | 3/2011 | Bedi et al. |
| 2011/0068148 A1 | 3/2011 | Hall et al. |
| 2011/0084113 A1 | 4/2011 | Bedi et al. |
| 2011/0084115 A1 | 4/2011 | Bedi et al. |
| 2011/0087276 A1 | 4/2011 | Bedi et al. |
| 2011/0114697 A1 | 5/2011 | Baxter, III et al. |
| 2011/0114698 A1 | 5/2011 | Baxter, III et al. |
| 2011/0114699 A1 | 5/2011 | Baxter, III et al. |
| 2011/0114700 A1 | 5/2011 | Baxter, III et al. |
| 2011/0118761 A1 | 5/2011 | Baxter, III et al. |
| 2011/0121051 A1 | 5/2011 | Shelton, IV et al. |
| 2011/0121052 A1 | 5/2011 | Shelton, IV et al. |
| 2011/0125176 A1 | 5/2011 | Yates et al. |
| 2011/0125177 A1 | 5/2011 | Yates et al. |
| 2011/0132962 A1 | 6/2011 | Hall et al. |
| 2011/0132963 A1 | 6/2011 | Giordano et al. |
| 2011/0132964 A1 | 6/2011 | Weisenburgh, II et al. |
| 2011/0132965 A1 | 6/2011 | Moore et al. |
| 2011/0139852 A1 | 6/2011 | Zingman |
| 2011/0144430 A1 | 6/2011 | Spivey et al. |
| 2011/0147433 A1 | 6/2011 | Shelton, IV et al. |
| 2011/0147434 A1 | 6/2011 | Hueil et al. |

FOREIGN PATENT DOCUMENTS

| | | |
|---|---|---|
| CA | 2512960 A1 | 1/2006 |
| CA | 2514274 A1 | 1/2006 |
| CN | 1915180 A | 2/2007 |
| DE | 273689 C | 5/1914 |
| DE | 1775926 A | 1/1972 |
| DE | 3210466 A1 | 9/1983 |
| DE | 9412228 U | 9/1994 |
| DE | 19509116 A1 | 9/1996 |
| DE | 19924311 A1 | 11/2000 |
| DE | 69328576 T2 | 1/2001 |
| DE | 10052679 A1 | 5/2001 |
| DE | 20112837 U1 | 10/2001 |
| DE | 20121753 U1 | 4/2003 |
| DE | 10314072 A1 | 10/2004 |
| DE | 202007003114 U1 | 6/2007 |
| EP | 0122046 A1 | 10/1984 |

| | | | | | | | |
|---|---|---|---|---|---|---|---|
| EP | 0070230 | B1 | 10/1985 | EP | 0908152 | B1 | 1/2002 |
| EP | 0387980 | B1 | 10/1985 | EP | 0872213 | B1 | 5/2002 |
| EP | 0033548 | B1 | 5/1986 | EP | 0862386 | B1 | 6/2002 |
| EP | 0276104 | A2 | 7/1988 | EP | 0949886 | B1 | 9/2002 |
| EP | 0248844 | B1 | 1/1993 | EP | 1238634 | A2 | 9/2002 |
| EP | 0277959 | B1 | 10/1993 | EP | 0858295 | B1 | 12/2002 |
| EP | 0233940 | B1 | 11/1993 | EP | 0656188 | B1 | 1/2003 |
| EP | 0261230 | B1 | 11/1993 | EP | 1284120 | A1 | 2/2003 |
| EP | 0639349 | A2 | 2/1994 | EP | 1287788 | A1 | 3/2003 |
| EP | 0324636 | B1 | 3/1994 | EP | 0717966 | B1 | 4/2003 |
| EP | 0593920 | A1 | 4/1994 | EP | 0869742 | B1 | 5/2003 |
| EP | 0523174 | B1 | 6/1994 | EP | 0829235 | B1 | 6/2003 |
| EP | 0600182 | A2 | 6/1994 | EP | 0887046 | B1 | 7/2003 |
| EP | 0310431 | B1 | 11/1994 | EP | 0852480 | B1 | 8/2003 |
| EP | 0375302 | B1 | 11/1994 | EP | 0891154 | B1 | 9/2003 |
| EP | 0376562 | B1 | 11/1994 | EP | 0813843 | B1 | 10/2003 |
| EP | 0630612 | A1 | 12/1994 | EP | 0873089 | B1 | 10/2003 |
| EP | 0634144 | A1 | 1/1995 | EP | 0856326 | B1 | 11/2003 |
| EP | 0646356 | A2 | 4/1995 | EP | 1374788 | A1 | 1/2004 |
| EP | 0646357 | A1 | 4/1995 | EP | 0741996 | B1 | 2/2004 |
| EP | 0653189 | A2 | 5/1995 | EP | 0814712 | B1 | 2/2004 |
| EP | 0669104 | A1 | 8/1995 | EP | 1402837 | A1 | 3/2004 |
| EP | 0511470 | B1 | 10/1995 | EP | 0705570 | B1 | 4/2004 |
| EP | 0679367 | A2 | 11/1995 | EP | 0959784 | B1 | 4/2004 |
| EP | 0392547 | B1 | 12/1995 | EP | 1407719 | A2 | 4/2004 |
| EP | 0685204 | A1 | 12/1995 | EP | 1086713 | B1 | 5/2004 |
| EP | 0364216 | B1 | 1/1996 | EP | 0996378 | B1 | 6/2004 |
| EP | 0699418 | A1 | 3/1996 | EP | 1426012 | A1 | 6/2004 |
| EP | 0702937 | A1 | 3/1996 | EP | 0833593 | B2 | 7/2004 |
| EP | 0705571 | A1 | 4/1996 | EP | 1442694 | A1 | 8/2004 |
| EP | 0711611 | A2 | 5/1996 | EP | 0888749 | B1 | 9/2004 |
| EP | 0484677 | B2 | 6/1996 | EP | 0959786 | B1 | 9/2004 |
| EP | 0541987 | B1 | 7/1996 | EP | 1459695 | A1 | 9/2004 |
| EP | 0667119 | B1 | 7/1996 | EP | 1473819 | A1 | 11/2004 |
| EP | 0708618 | B1 | 3/1997 | EP | 1477119 | A1 | 11/2004 |
| EP | 0770355 | A1 | 5/1997 | EP | 1479345 | A1 | 11/2004 |
| EP | 0503662 | B1 | 6/1997 | EP | 1479347 | A1 | 11/2004 |
| EP | 0447121 | B1 | 7/1997 | EP | 1479348 | A1 | 11/2004 |
| EP | 0625077 | B1 | 7/1997 | EP | 0754437 | B2 | 12/2004 |
| EP | 0633749 | B1 | 8/1997 | EP | 1025807 | B1 | 12/2004 |
| EP | 0710090 | B1 | 8/1997 | EP | 1001710 | B1 | 1/2005 |
| EP | 0578425 | B1 | 9/1997 | EP | 1520521 | A1 | 4/2005 |
| EP | 0625335 | B1 | 11/1997 | EP | 1520523 | A1 | 4/2005 |
| EP | 0552423 | B1 | 1/1998 | EP | 1520525 | A1 | 4/2005 |
| EP | 0592244 | B1 | 1/1998 | EP | 1522264 | A1 | 4/2005 |
| EP | 0648476 | B1 | 1/1998 | EP | 1523942 | A2 | 4/2005 |
| EP | 0649290 | B1 | 3/1998 | EP | 1550408 | A1 | 7/2005 |
| EP | 0598618 | B1 | 9/1998 | EP | 1557129 | A1 | 7/2005 |
| EP | 0676173 | B1 | 9/1998 | EP | 1064883 | B1 | 8/2005 |
| EP | 0678007 | B1 | 9/1998 | EP | 1067876 | B1 | 8/2005 |
| EP | 0603472 | B1 | 11/1998 | EP | 0870473 | B1 | 9/2005 |
| EP | 0605351 | B1 | 11/1998 | EP | 1157666 | B1 | 9/2005 |
| EP | 0878169 | A1 | 11/1998 | EP | 0880338 | B1 | 10/2005 |
| EP | 0879742 | A1 | 11/1998 | EP | 1158917 | B1 | 11/2005 |
| EP | 0695144 | B1 | 12/1998 | EP | 1344498 | B1 | 11/2005 |
| EP | 0722296 | B1 | 12/1998 | EP | 1330989 | B1 | 12/2005 |
| EP | 0760230 | B1 | 2/1999 | EP | 0771176 | B2 | 1/2006 |
| EP | 0623316 | B1 | 3/1999 | EP | 1621138 | A2 | 2/2006 |
| EP | 0650701 | B1 | 3/1999 | EP | 1621139 | A2 | 2/2006 |
| EP | 0537572 | B1 | 6/1999 | EP | 1621141 | A2 | 2/2006 |
| EP | 0923907 | A1 | 6/1999 | EP | 1621145 | A2 | 2/2006 |
| EP | 0843906 | B1 | 3/2000 | EP | 1621151 | A2 | 2/2006 |
| EP | 0552050 | B1 | 5/2000 | EP | 1034746 | B1 | 3/2006 |
| EP | 0833592 | B1 | 5/2000 | EP | 1632191 | A2 | 3/2006 |
| EP | 0830094 | B1 | 9/2000 | EP | 1065981 | B1 | 5/2006 |
| EP | 1034747 | A1 | 9/2000 | EP | 1082944 | B1 | 5/2006 |
| EP | 1034748 | A1 | 9/2000 | EP | 1652481 | A2 | 5/2006 |
| EP | 0694290 | B1 | 11/2000 | EP | 1382303 | B1 | 6/2006 |
| EP | 1050278 | A1 | 11/2000 | EP | 1253866 | B1 | 7/2006 |
| EP | 1053719 | A1 | 11/2000 | EP | 1032318 | B1 | 8/2006 |
| EP | 1053720 | A1 | 11/2000 | EP | 1045672 | B1 | 8/2006 |
| EP | 1055399 | A1 | 11/2000 | EP | 1617768 | B1 | 8/2006 |
| EP | 1055400 | A1 | 11/2000 | EP | 1693015 | A2 | 8/2006 |
| EP | 1080694 | A1 | 3/2001 | EP | 1400214 | B1 | 9/2006 |
| EP | 1090592 | A1 | 4/2001 | EP | 1702567 | A2 | 9/2006 |
| EP | 1095627 | A1 | 5/2001 | EP | 1129665 | B1 | 11/2006 |
| EP | 1256318 | B1 | 5/2001 | EP | 1400206 | B1 | 11/2006 |
| EP | 0806914 | B1 | 9/2001 | EP | 1256317 | B1 | 12/2006 |
| EP | 0768840 | B1 | 12/2001 | EP | 1728473 | A1 | 12/2006 |

| | | | | | | |
|---|---|---|---|---|---|---|
| EP | 1728475 | A2 | 12/2006 | SU | 886900 | A1 | 12/1981 |
| EP | 1479346 | B1 | 1/2007 | SU | 1333319 | A2 | 8/1987 |
| EP | 1484024 | B1 | 1/2007 | SU | 1561964 | A1 | 5/1990 |
| EP | 1754445 | A2 | 2/2007 | SU | 1722476 | A1 | 3/1992 |
| EP | 1759812 | A1 | 3/2007 | SU | 1377053 | A1 | 2/1998 |
| EP | 1767163 | A1 | 3/2007 | WO | WO 91/15157 | A1 | 10/1991 |
| EP | 1769756 | A1 | 4/2007 | WO | WO 92/21300 | A1 | 12/1992 |
| EP | 1769758 | A1 | 4/2007 | WO | WO 93/08755 | A1 | 5/1993 |
| EP | 1581128 | B1 | 5/2007 | WO | WO 93/13718 | A1 | 7/1993 |
| EP | 1785097 | A2 | 5/2007 | WO | WO 93/14690 | A1 | 8/1993 |
| EP | 1790293 | A2 | 5/2007 | WO | WO 93/15850 | A1 | 8/1993 |
| EP | 1800610 | A1 | 6/2007 | WO | WO 93/19681 | A1 | 10/1993 |
| EP | 1300117 | B1 | 8/2007 | WO | WO 94/00060 | A1 | 1/1994 |
| EP | 1813199 | A1 | 8/2007 | WO | WO 94/11057 | A1 | 5/1994 |
| EP | 1813201 | A1 | 8/2007 | WO | WO 94/12108 | A1 | 6/1994 |
| EP | 1813203 | A2 | 8/2007 | WO | WO 94/18893 | A1 | 9/1994 |
| EP | 1813207 | A1 | 8/2007 | WO | WO 94/22378 | A1 | 10/1994 |
| EP | 1813209 | A1 | 8/2007 | WO | WO 94/23659 | A1 | 10/1994 |
| EP | 1487359 | B1 | 10/2007 | WO | WO 95/02369 | A1 | 1/1995 |
| EP | 1599146 | B1 | 10/2007 | WO | WO 95/03743 | A1 | 2/1995 |
| EP | 1402821 | B1 | 12/2007 | WO | WO 95/06817 | A1 | 3/1995 |
| EP | 1872727 | A1 | 1/2008 | WO | WO 95/09576 | A1 | 4/1995 |
| EP | 1839596 | A2 | 2/2008 | WO | WO 95/09577 | A1 | 4/1995 |
| EP | 1897502 | A1 | 3/2008 | WO | WO 95/14436 | A1 | 6/1995 |
| EP | 1330201 | B1 | 6/2008 | WO | WO 95/17855 | A1 | 7/1995 |
| EP | 1702568 | B1 | 7/2008 | WO | WO 95/18383 | A1 | 7/1995 |
| EP | 1943976 | A2 | 7/2008 | WO | WO 95/18572 | A1 | 7/1995 |
| EP | 1593337 | B1 | 8/2008 | WO | WO 95/19739 | A1 | 7/1995 |
| EP | 1970014 | A1 | 9/2008 | WO | WO 95/20360 | A1 | 8/1995 |
| EP | 1980213 | A2 | 10/2008 | WO | WO 95/23557 | A1 | 9/1995 |
| EP | 1759645 | B1 | 11/2008 | WO | WO 95/24865 | A1 | 9/1995 |
| EP | 1693008 | 81 | 12/2008 | WO | WO 95/25471 | A3 | 9/1995 |
| EP | 1759640 | B1 | 12/2008 | WO | WO 95/26562 | A1 | 10/1995 |
| EP | 2000102 | A2 | 12/2008 | WO | WO 95/29639 | A1 | 11/1995 |
| EP | 1749486 | B1 | 3/2009 | WO | WO 96/04858 | A1 | 2/1996 |
| EP | 1721576 | B1 | 4/2009 | WO | WO 96/19151 | A1 | 6/1996 |
| EP | 2090256 | A2 | 8/2009 | WO | WO 96/19152 | A1 | 6/1996 |
| EP | 1607050 | B1 | 12/2009 | WO | WO 96/20652 | A1 | 7/1996 |
| EP | 1566150 | B1 | 4/2010 | WO | WO 96/21119 | A1 | 7/1996 |
| EP | 1813206 | B1 | 4/2010 | WO | WO 96/22055 | A1 | 7/1996 |
| EP | 1769754 | B1 | 6/2010 | WO | WO 96/23448 | A1 | 8/1996 |
| EP | 1535565 | B1 | 10/2010 | WO | WO 96/24301 | A1 | 8/1996 |
| EP | 1702570 | B1 | 10/2010 | WO | WO 96/27337 | A1 | 9/1996 |
| FR | 999646 | A | 2/1952 | WO | WO 96/35464 | A1 | 11/1996 |
| FR | 1112936 | A | 3/1956 | WO | WO 96/39085 | A1 | 12/1996 |
| FR | 2765794 | A | 1/1999 | WO | WO 96/39086 | A1 | 12/1996 |
| GB | 939929 | A | 10/1963 | WO | WO 96/39087 | A1 | 12/1996 |
| GB | 1210522 | A | 10/1970 | WO | WO 96/39088 | A1 | 12/1996 |
| GB | 1217159 | A | 12/1970 | WO | WO 96/39089 | A1 | 12/1996 |
| GB | 2109241 | A | 6/1983 | WO | WO 97/00646 | A1 | 1/1997 |
| GB | 2272159 | A | 5/1994 | WO | WO 97/00647 | A1 | 1/1997 |
| GB | 2284242 | A | 5/1995 | WO | WO 97/06582 | A1 | 2/1997 |
| GB | 2336214 | A | 10/1999 | WO | WO 97/10763 | A1 | 3/1997 |
| GB | 2425903 | A | 11/2006 | WO | WO 97/10764 | A1 | 3/1997 |
| JP | 6007357 | A | 1/1994 | WO | WO 97/11648 | A2 | 4/1997 |
| JP | 7051273 | A | 2/1995 | WO | WO 97/11649 | A1 | 4/1997 |
| JP | 8033641 | A | 2/1996 | WO | WO 97/15237 | A1 | 5/1997 |
| JP | 8229050 | A | 9/1996 | WO | WO 97/24073 | A1 | 7/1997 |
| JP | 2000033071 | A | 2/2000 | WO | WO 97/24993 | A1 | 7/1997 |
| JP | 2000171730 | A | 6/2000 | WO | WO 97/30644 | A1 | 8/1997 |
| JP | 2000287987 | A | 10/2000 | WO | WO 97/34533 | A1 | 9/1997 |
| JP | 2000325303 | A | 11/2000 | WO | WO 97/37598 | A1 | 10/1997 |
| JP | 2001286477 | A | 10/2001 | WO | WO 97/39688 | A2 | 10/1997 |
| JP | 2002143078 | A | 5/2002 | WO | WO 98/17180 | A1 | 4/1998 |
| JP | 2002369820 | A | 12/2002 | WO | WO 98/27880 | A1 | 7/1998 |
| JP | 2005505322 | T | 2/2005 | WO | WO 98/30153 | A1 | 7/1998 |
| JP | 2005103293 | A | 4/2005 | WO | WO 98/47436 | A1 | 10/1998 |
| JP | 2005131163 | A | 5/2005 | WO | WO 99/03407 | A1 | 1/1999 |
| JP | 2005131164 | A | 5/2005 | WO | WO 99/03408 | A1 | 1/1999 |
| JP | 2005131173 | A | 5/2005 | WO | WO 99/03409 | A1 | 1/1999 |
| JP | 2005131211 | A | 5/2005 | WO | WO 99/12483 | A1 | 3/1999 |
| JP | 2005131212 | A | 5/2005 | WO | WO 99/12487 | A1 | 3/1999 |
| JP | 2005137423 | A | 6/2005 | WO | WO 99/12488 | A1 | 3/1999 |
| JP | 2005152416 | A | 6/2005 | WO | WO 99/15086 | A1 | 4/1999 |
| JP | 2006-281405 | A | 10/2006 | WO | WO 99/15091 | A1 | 4/1999 |
| RU | 2187249 | C2 | 8/2002 | WO | WO 99/23933 | A2 | 5/1999 |
| RU | 2225170 | C2 | 3/2004 | WO | WO 99/23959 | A1 | 5/1999 |
| SU | 189517 | A | 1/1967 | WO | WO 99/25261 | A1 | 5/1999 |
| SU | 328636 | A | 9/1972 | WO | WO 99/29244 | A1 | 6/1999 |

| | | |
|---|---|---|
| WO | WO 99/34744 A1 | 7/1999 |
| WO | WO 99/45849 A1 | 9/1999 |
| WO | WO 99/48430 A1 | 9/1999 |
| WO | WO 99/51158 A1 | 10/1999 |
| WO | WO 00/24322 A1 | 5/2000 |
| WO | WO 00/24330 A1 | 5/2000 |
| WO | WO 00/41638 A1 | 7/2000 |
| WO | WO 00/48506 A1 | 8/2000 |
| WO | WO 00/53112 A2 | 9/2000 |
| WO | WO 00/54653 A1 | 9/2000 |
| WO | WO 00/057796 A1 | 10/2000 |
| WO | WO 00/64365 A1 | 11/2000 |
| WO | WO 00/72762 A1 | 12/2000 |
| WO | WO 00/72765 A1 | 12/2000 |
| WO | WO 01/03587 A1 | 1/2001 |
| WO | WO 01/05702 A1 | 1/2001 |
| WO | WO 01/10482 A1 | 2/2001 |
| WO | WO 01/35845 A1 | 5/2001 |
| WO | WO 01/54594 A1 | 8/2001 |
| WO | WO 01/58371 A1 | 8/2001 |
| WO | WO 01/62158 A2 | 8/2001 |
| WO | WO 01/62161 A1 | 8/2001 |
| WO | WO 01/62162 A1 | 8/2001 |
| WO | WO 01/62164 A2 | 8/2001 |
| WO | WO 01/62169 A2 | 8/2001 |
| WO | WO 01/78605 A2 | 10/2001 |
| WO | WO 01/91646 A1 | 12/2001 |
| WO | WO 02/07608 A2 | 1/2002 |
| WO | WO 02/07618 A1 | 1/2002 |
| WO | WO 02/17799 A1 | 3/2002 |
| WO | WO 02/19920 A1 | 3/2002 |
| WO | WO 02/19932 A1 | 3/2002 |
| WO | WO 02/30297 A2 | 4/2002 |
| WO | WO 02/32322 A2 | 4/2002 |
| WO | WO 02/36028 A1 | 5/2002 |
| WO | WO 02/43571 A2 | 6/2002 |
| WO | WO 02/058568 A1 | 8/2002 |
| WO | WO 02/060328 A1 | 8/2002 |
| WO | WO 02/067785 A2 | 9/2002 |
| WO | WO 02/098302 A1 | 12/2002 |
| WO | WO 03/000138 A2 | 1/2003 |
| WO | WO 03/001329 A2 | 1/2003 |
| WO | WO 03/013363 A1 | 2/2003 |
| WO | WO 03/015604 A2 | 2/2003 |
| WO | WO 03/020106 A2 | 3/2003 |
| WO | WO 03/020139 A2 | 3/2003 |
| WO | WO 03/024339 A1 | 3/2003 |
| WO | WO 03/079909 A3 | 3/2003 |
| WO | WO 03/030743 A2 | 4/2003 |
| WO | WO 03/037193 A1 | 5/2003 |
| WO | WO 03/047436 A3 | 6/2003 |
| WO | WO 03/055402 A1 | 7/2003 |
| WO | WO 03/057048 A1 | 7/2003 |
| WO | WO 03/057058 A1 | 7/2003 |
| WO | WO 03/063694 A1 | 8/2003 |
| WO | WO 03/077769 A1 | 9/2003 |
| WO | WO 03/079911 A1 | 10/2003 |
| WO | WO 03/082126 A1 | 10/2003 |
| WO | WO 03/088845 A2 | 10/2003 |
| WO | WO 03/090630 A2 | 11/2003 |
| WO | WO 03/094743 A1 | 11/2003 |
| WO | WO 03/094745 A1 | 11/2003 |
| WO | WO 03/094746 A1 | 11/2003 |
| WO | WO 03/094747 A1 | 11/2003 |
| WO | WO 03/101313 A1 | 12/2003 |
| WO | WO 03/105698 A2 | 12/2003 |
| WO | WO 03/105702 A2 | 12/2003 |
| WO | WO 2004/006980 A2 | 1/2004 |
| WO | WO 2004/019769 A1 | 3/2004 |
| WO | WO 2004/021868 A2 | 3/2004 |
| WO | WO 2004/028585 A2 | 4/2004 |
| WO | WO 2004/032754 A2 | 4/2004 |
| WO | WO 2004/032760 A2 | 4/2004 |
| WO | WO 2004/032762 A1 | 4/2004 |
| WO | WO 2004/032763 A2 | 4/2004 |
| WO | WO 2004/034875 A2 | 4/2004 |
| WO | WO 2004/047626 A1 | 6/2004 |
| WO | WO 2004/047653 A2 | 6/2004 |
| WO | WO 2004/049956 A2 | 6/2004 |
| WO | WO 2004/052426 A2 | 6/2004 |
| WO | WO 2004/056276 A1 | 7/2004 |
| WO | WO 2004/056277 A1 | 7/2004 |
| WO | WO 2004/062516 A1 | 7/2004 |
| WO | WO 2004/078050 A2 | 9/2004 |
| WO | WO 2004/078051 A2 | 9/2004 |
| WO | WO 2004/086987 A1 | 10/2004 |
| WO | WO 2004/096015 A2 | 11/2004 |
| WO | WO 2004/096057 A2 | 11/2004 |
| WO | WO 2004/103157 A2 | 12/2004 |
| WO | WO 2004/105593 A1 | 12/2004 |
| WO | WO 2004/105621 A1 | 12/2004 |
| WO | WO 2004/112618 A2 | 12/2004 |
| WO | WO 2004/112652 A2 | 12/2004 |
| WO | WO 2005/027983 A2 | 3/2005 |
| WO | WO 2005/037329 A2 | 4/2005 |
| WO | WO 2005/044078 A2 | 5/2005 |
| WO | WO 2005/055846 A1 | 6/2005 |
| WO | WO 2005/072634 A2 | 8/2005 |
| WO | WO 2005/078892 A1 | 8/2005 |
| WO | WO 2005/096954 A2 | 10/2005 |
| WO | WO 2005/112806 A2 | 12/2005 |
| WO | WO 2005/112808 A1 | 12/2005 |
| WO | WO 2005/115251 A2 | 12/2005 |
| WO | WO 2005/117735 A1 | 12/2005 |
| WO | WO 2005/122936 A1 | 12/2005 |
| WO | WO 2006/044490 A2 | 4/2006 |
| WO | WO 2006/044581 A2 | 4/2006 |
| WO | WO 2006/044810 A2 | 4/2006 |
| WO | WO 2006/051252 A1 | 5/2006 |
| WO | WO 2006/059067 A1 | 6/2006 |
| WO | WO 2006/083748 A1 | 8/2006 |
| WO | WO 2006/092563 A1 | 9/2006 |
| WO | WO 2006/092565 A1 | 9/2006 |
| WO | WO 2006/115958 A1 | 11/2006 |
| WO | WO 2006/125940 A1 | 11/2006 |
| WO | WO 2006/132992 A1 | 12/2006 |
| WO | WO 2007/002180 A2 | 1/2007 |
| WO | WO 2007/016290 A2 | 2/2007 |
| WO | WO 2007/018898 A2 | 2/2007 |
| WO | WO 2007/098220 A2 | 8/2007 |
| WO | WO 2007/121579 A1 | 11/2007 |
| WO | WO 2007/137304 A2 | 11/2007 |
| WO | WO 2007/139734 A2 | 12/2007 |
| WO | WO 2007/142625 A2 | 12/2007 |
| WO | WO 2008/021969 A2 | 2/2008 |
| WO | WO 2008/039270 A1 | 4/2008 |
| WO | WO 2008/045383 A2 | 4/2008 |
| WO | WO 2008/109125 A1 | 9/2008 |

OTHER PUBLICATIONS

C.C. Thompson et al., "Peroral Endoscopic Reduction of Dilated Gastrojejunal Anastomosis After Roux-en-Y Gastric Bypass: A Possible New Option for Patients with Weight Regain," Surg Endosc (2006) vol. 20, pp. 1744-1748.
B.R. Coolman, DVM, MS et al., "Comparison of Skin Staples With Sutures for Anastomosis of the Small Intestine in Dogs," Abstract; http://www.blackwell-synergy.com/doi/abs/10.1053/jvet.2000. 7539?cookieSet=1&journalCode=vsu which redirects to http://www3.interscience.wiley.com/journal/119040681/abstract?CRETRY=1&SRETRY=0; [online] accessed: Sep. 22, 2008 (2 pages).
The Sodem Aseptic Battery Transfer Kit, Sodem Systems, 2000, 3 pages.
"Biomedical Coatings," Fort Wayne Metals, Research Products Corporation, obtained online at www.fwmetals.com on Jun. 21, 2010 (1 page).
European Search Report, Application No. 10250541.9, dated Jul. 13, 2010 (5 pages).
Van Meer et al., "A Disposable Plastic Compact Wrist for Smart Minimally invasive Surgical Tools," LAAS/CNRS (Aug. 2005).
Breedveld et al., "A New, Easily Miniaturized Sterrable Endoscope," IEEE Engineering in Medicine and Biology Magazine (Nov./Dec. 2005).
D. Tuite, Ed., "Get The Lowdown On Ultracapacitors," Nov. 15, 2007; [online] URL: http://electronicdesign.com/Articles/Print.cfm?ArticleID=17465, accessed Jan. 15, 2008 (5 pages).

* cited by examiner

CIRCULAR SURGICAL STAPLING INSTRUMENT WITH ANVIL LOCKING SYSTEM

FIELD OF THE INVENTION

The present invention generally relates to surgical staplers, and more particularly, to an anvil locking system for locking an anvil of a circular stapling instrument in place.

BACKGROUND

In certain types of surgical procedures, the use of surgical staples has become the preferred method of joining tissue and, as such, specially configured surgical staplers have been developed for these applications. For example, intra-luminal or circular staplers have been developed for use in a surgical procedure known as an anastomosis. Circular staplers useful for performing an anastomosis are disclosed, for example, in U.S. Pat. Nos. 5,104,025; 5,205,459; 5,285,945; and 5,309,927 which are each herein incorporated by reference in their respective entireties.

One form of an anastomosis comprises a surgical procedure wherein sections of intestine are joined together after a diseased portion has been excised. The procedure requires re-joining the ends of the two tubular sections together to form a continuous tubular pathway. Previously, this surgical procedure was a laborious and time consuming operation. The surgeon had to precisely cut and align the ends of the intestine and maintain the alignment while joining the ends with numerous suture stitches. The development of circular staplers has greatly simplified the anastomosis procedure and also decreased the time required to perform an anastomosis.

In general, a conventional circular stapler typically consists of an elongated shaft that has a proximal actuating mechanism and a distal stapling mechanism mounted to the shaft. The distal stapling mechanism commonly consists of a fixed stapling cartridge that contains a plurality of staples configured in a concentric circular array. A round cutting knife is concentrically mounted in the cartridge interior to the staples for axial travel therein. Extending axially from the center of the cartridge is a movable trocar shaft that is adapted to have a staple anvil removably coupled thereto. The anvil is configured to form the ends of the staples as they are driven into it. The distance between a distal face of the staple cartridge and the staple anvil is controlled by an adjustment mechanism mounted to the proximal end of the stapler shaft for controlling the axial movement of the trocar. Tissue clamped between the staple cartridge and the staple anvil is simultaneously stapled and cut when the actuating mechanism is activated by the surgeon.

When performing an anastomosis using a circular stapler, the intestine is typically stapled using a conventional surgical stapler with double rows of staples being emplaced on either side of the diseased portion of intestine to be removed. The target section is simultaneously cut as the adjoining end is stapled. After removing the diseased portion, the surgeon typically inserts the anvil into the proximal end of the lumen, proximal of the staple line. This is done by inserting the anvil head into an entry port cut into the proximal lumen by the surgeon. On occasion, the anvil can be placed transanally, by placing the anvil head on the distal end of the stapler and inserting the instrument through the rectum. The surgeon then ties the proximal end of the intestine to the anvil shaft using a suture or other conventional tying device. Next, the surgeon cuts excess tissue adjacent to the tie and the surgeon attaches the anvil to the trocar shaft of the stapler. The surgeon then closes the gap between the anvil and cartridge, thereby clamping the proximal and distal ends of the intestine in the gap. The surgeon next actuates the stapler causing several rows of staples to be driven through both ends of the intestine and formed, thereby joining the ends and forming a tubular pathway. Simultaneously, as the staples are driven and formed, the concentric circular knife blade is driven through the intestinal tissue ends, cutting the ends adjacent to the inner row of staples. The surgeon then withdraws the stapler from the intestine and the anastomosis is complete.

During the above-described surgical procedures, the clinician generally strives to obtain a tight enough staple line to prevent leakage and bleeding and to achieve "tissue-to-tissue" contact which promotes tissue healing. In general, by controlling the amount of compression that is applied to the tissue, better stapling and healing results will be achieved. Achieving a desired amount of tissue compression becomes challenging when dealing with thick tissues and thin tissues. For example, when stapling thinner tissue, it is necessary to move to the lower end of the compression range to obtain compression of the tissue—without over compressing it. When stapling thicker tissues, the proper compression will be achieved at a larger gap setting.

A simple robust means to measure this compression would be to use a compliant member and an indicator to measure displacement similar to a spring force scale. Such arrangements, however, must be able to withstand the forces required to form the staples and to cut through a break away washer which is commonly mounted in the anvil. In some instances, for example, such forces may exceed 300 lbf and must be restrained without deflection to ensure the proper formed staple height is achieved. Such devices, however, present additional challenges to the user. In particular, once the anvil has been properly positioned, it is necessary that the anvil not move during firing. Those anvil systems that are compliant in nature may facilitate undesirable movement or deflection of the anvil during firing which could adversely affect proper staple formation.

Thus, the need exists for an anvil locking system that can be used to selectively retain the anvil in a desired position during stapling.

The foregoing discussion is intended only to illustrate some of the shortcomings present in the field of the invention at the time, and should not be taken as a disavowal of claim scope.

BRIEF SUMMARY

The invention overcomes the above-noted and other deficiencies of the prior art by providing a surgical stapling instrument for applying one or more surgical staples to tissue. Various embodiments comprise a handle assembly and a shaft assembly that is coupled to the handle assembly. A stapling head assembly may be operably coupled to the shaft assembly. The stapling head assembly may comprise a staple cartridge for supporting one or more surgical staples, a staple driver for engaging and driving the staples from the staple cartridge, and a knife that is movably supported in the stapling head assembly. The surgical stapling instrument may further include a drive system for applying drive motions to the staple driver and the knife. An anvil is movably supported relative to the staple cartridge for axial movement toward and away from the staple cartridge. The instrument may also include an anvil adjustment assembly for selectively adjusting an axial position of the anvil relative to the staple cartridge. The instrument also comprises an anvil locking system configured to cooperate with the anvil adjustment assembly to selectively lock and unlock the anvil in axial position relative to the staple cartridge.

In another general aspect of the present invention, there is provided a surgical stapling instrument for applying one or more surgical staples to tissue. Various embodiments may comprise a handle assembly and a stapling head assembly that is operably coupled to the handle assembly. An anvil is movably supported relative to the stapling head assembly for selective axial travel toward and away from the stapling head assembly. An anvil adjustment assembly is supported by the handle assembly for selectively adjusting an axial position of the anvil relative to the staple cartridge. An anvil locking system is configured to cooperate with the anvil adjustment assembly to selectively lock and unlock the anvil in axial positions relative to the stapling head.

BRIEF DESCRIPTION OF THE FIGURES

The accompanying drawings, which are incorporated in and constitute a part of this specification, illustrate embodiments of the invention, and, together with the general description of the invention given above, and the detailed description of the embodiments given below, serve to explain the principles of the present invention.

DETAILED DESCRIPTION

Certain exemplary embodiments will now be described to provide an overall understanding of the principles of the structure, function, manufacture, and use of the devices and methods disclosed herein. One or more examples of these embodiments are illustrated in the accompanying drawings. Those of ordinary skill in the art will understand that the devices and methods specifically described herein and illustrated in the accompanying drawings are non-limiting exemplary embodiments and that the scope of the various embodiments of the present invention is defined solely by the claims. The features illustrated or described in connection with one exemplary embodiment may be combined with the features of other embodiments. Such modifications and variations are intended to be included within the scope of the present invention.

Turning to the Drawings, wherein like numerals denote like components, there is shown a circular stapler 10 that includes a unique and novel system for locking the anvil in position while the stapler is being actuated to cut tissue and simultaneously form staples in the adjacent tissue. One form of circular stapler that may employ the anvil locking system embodiments of the present invention is disclosed in U.S. Patent Publication No. US 2008/0078806A1, the disclosure of which is herein incorporated by reference in its entirety. However, as the present Detailed Description proceeds, those of ordinary skill in the art will readily appreciate that the various anvil locking system embodiments of the present invention may be successfully employed with various other circular stapler configurations without departing from the spirit and scope of the present invention.

The terms "proximal" and "distal" are used herein with reference to a clinician manipulating the handle portion of the surgical instrument. The term "proximal" referring to the portion closest to the clinician and the term "distal" referring to the portion located away from the clinician. It will be further appreciated that, for convenience and clarity, spatial terms such as "vertical", "horizontal", "up" and "down" may be used herein with respect to the drawings. However, surgical instruments are used in many orientations and positions, and these terms are not intended to be limiting and/or absolute.

Figure 1:
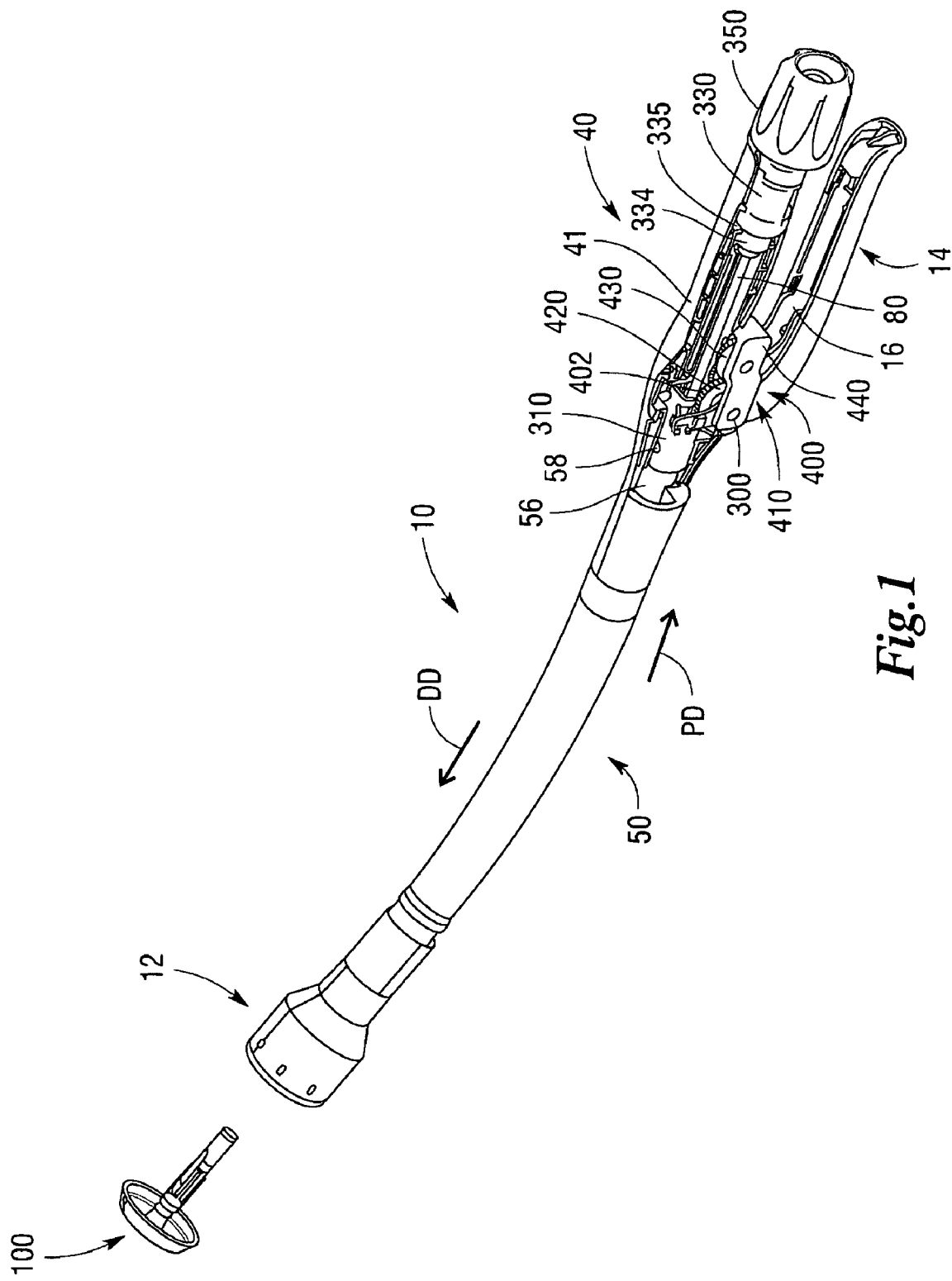
FIG. 1 is a perspective view of a surgical stapling instrument embodiment of the present invention with a portion of the handle housing removed.

As can be seen in FIG. 1, there is disclosed a circular stapler 10 that includes a stapling head assembly 12, an anvil 100, an adjustment knob 350, and a trigger 14. The stapling head assembly 12 is coupled to a handle assembly 40 by a shaft assembly 50. When the trigger 14 is activated, a drive system operates within the shaft assembly 50 so that staples 90 (FIG. 2) are expelled from the stapling head assembly 12 into forming contact with the anvil 100. Simultaneously, a knife 70, that is operably supported within the head 12, acts to cut tissue held within the circumference of the stapled tissue. The stapler 10 is then pulled through the tissue leaving stapled tissue in its place.

Figure 2:
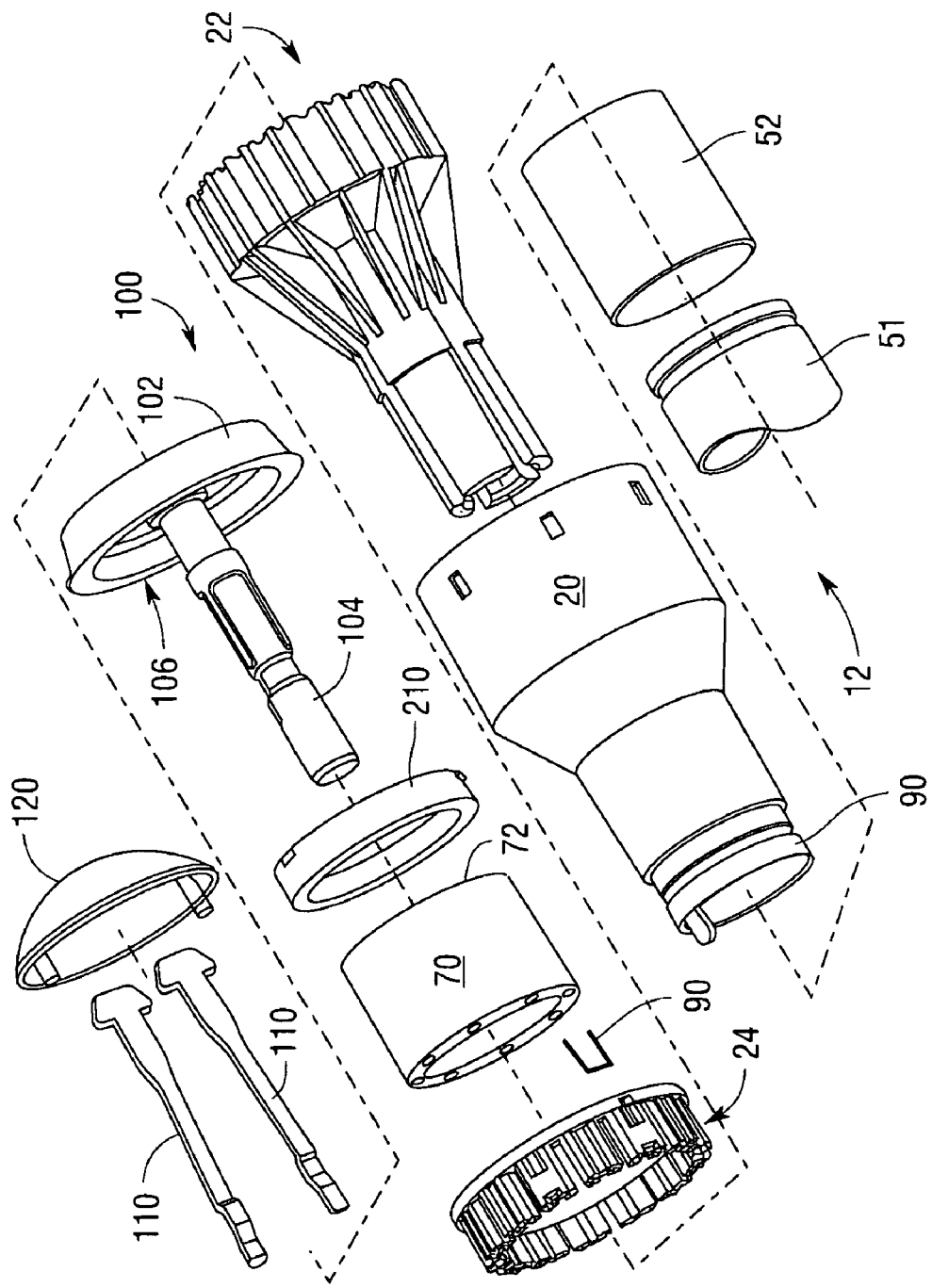
FIG. 2 is an exploded assembly view of the staple head assembly of the surgical stapling instrument depicted in FIG. 1.

FIG. 2 illustrates one form of anvil 100 and stapling head assembly 12 that may be employed in connection with various embodiments of the subject invention. As can be seen in that Figure, the anvil 100 may have a circular body portion 102 that has an anvil shaft 104 for attaching a trocar 60 (FIG. 3) thereto. The anvil body 102 has a staple forming undersurface 106 thereon. In various embodiments, a shroud 120 is attached to the distal end of the anvil body 102. The anvil 100 may be further provided with a pair of trocar retaining clips or leaf-type springs 110 that serve to releasable retain the trocar 60 in retaining engagement with the anvil shaft 104.

As can also be seen in FIG. 2, the stapling head assembly 12 may comprise a casing member 20 that supports a cartridge supporting assembly in the form of a staple driver 22 that is adapted to interface with a circular staple cartridge 24 and drive staples 90 supported therein into forming contact with the staple forming undersurface 106 of anvil 100. A circular knife 70 is centrally disposed within the staple driver 22 and has a distal cutting edge 72 formed thereon. The proximal end 21 of the casing member 20 may be coupled to an outer tubular shroud 51 of the shaft assembly 50 by a distal ferrule member 52.

Figure 3:
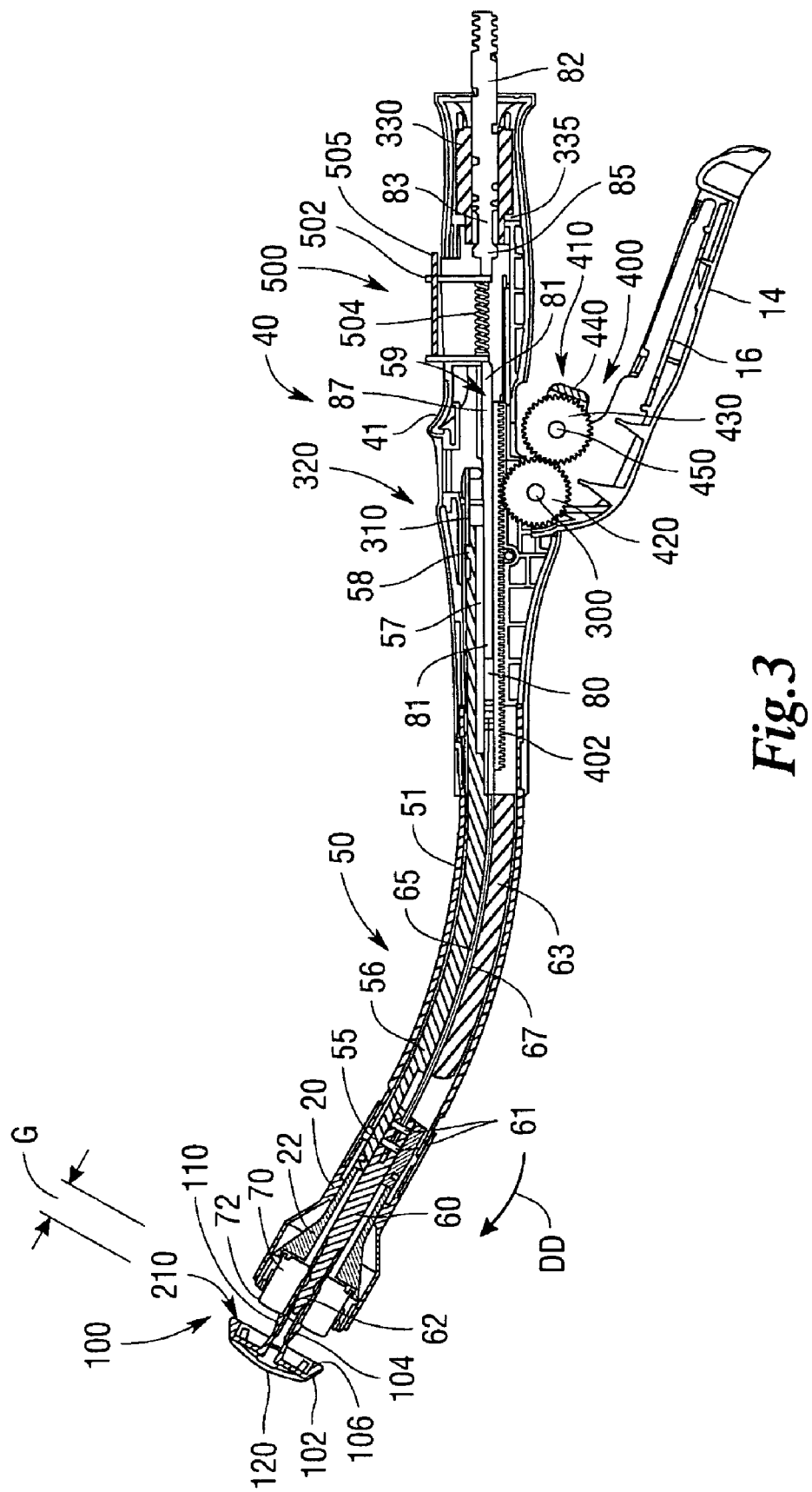
FIG. 3 is a cross-sectional view of a portion of the surgical stapling instrument of FIG. 1 with the anvil locking system in an unlocked position.

FIG. 3 illustrates a shaft assembly 50 that operably supports the trocar 60 and compression shaft 54 for axial movement therein. The compression shaft 54 may be axially and movably supported within the outer tubular shroud 51 and include a distal compression shaft portion 55. As can also be seen in FIG. 3, the distal compression shaft portion 55 is coupled to the staple driver 22. Thus, axial movement of the compression shaft portion 55 within the outer tubular shroud 51 causes the staple driver 22 to move axially within the casing member 20. Actuation of the firing trigger 14 will cause the compression shaft 54 and the distal compression shaft portion 55 to move in the distal direction (arrow "DD") thereby driving the staple driver 22 distally to fire the staples 90 into forming contact with the staple forming undersurface 106 of the anvil 100. As the staple driver 22 is driven distally, it also drives the cutting edge 72 of the knife 70 through the tissue held within the circumference of the stapled tissue into a knife board 210 mounted in the anvil 100.

The anvil adjustment assembly, generally designated as 59, includes the trocar 60 and related structure employed to axially move the trocar 60 (and the anvil 100 when attached thereto) relative to the stapling head assembly 12. The trocar 60 may include a trocar tip 62 that has attached thereto a top tension band 65 and a bottom tension band 67. The trocar tip 62 may be coupled to the top tension band 65 and bottom tension band 67 by fasteners 61 (e.g., screws, studs, posts, etc.). A spacer band 63 may be received within the tubular shroud 51 and serves to slidably support the upper and lower tension bands 65, 67 within the shroud 51. The proximal ends of the top tension band 65 and bottom tension band 67 may be attached to a distal end of an adjustment shaft 80. As illustrated in FIG. 3, the tip 62 of the trocar 60 may be inserted into the anvil shaft 104 of the anvil 100 and retained in engagement by the trocar retaining clips 110.

Figure 4:
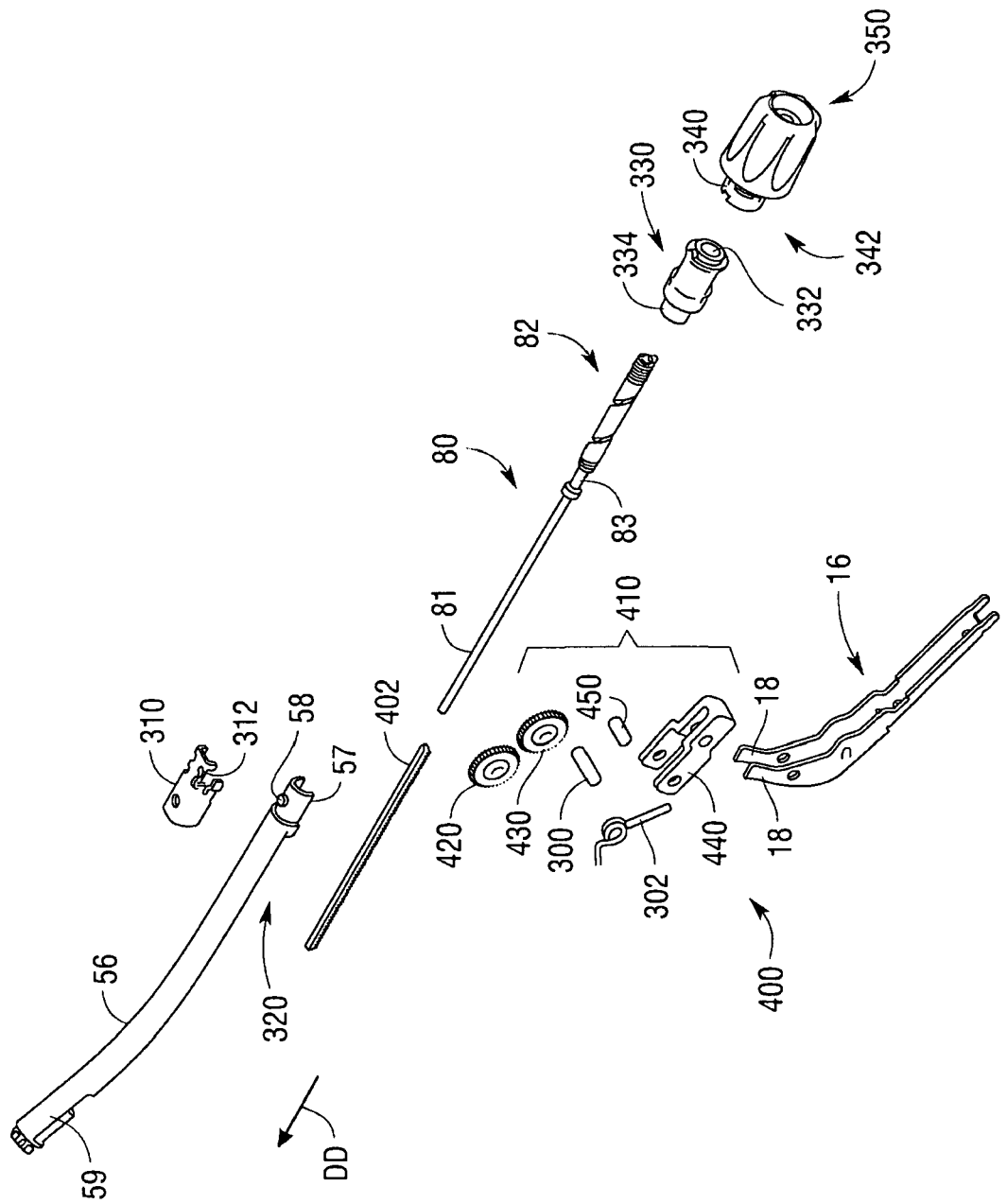
FIG. 4 is an exploded assembly view of the surgical stapling instrument of FIGS. 1 and 3.

In various embodiments, the adjusting shaft 80 is axially movably supported within a handle assembly 40 that may comprise two handle casing segments 41 that are interconnected together by suitable fastener arrangements for ease of assembly. The trigger 14 is pivotally attached to the handle assembly 40 by a pivot pin 300. A spring 302 is supported on pivot pin 300 and serves to bias the trigger 14 away from the handle assembly 40 to an unactuated position. As can be seen in FIG. 4, the trigger 14 may comprise a trigger frame member 16 that has a pair of fins 18 that are sized to be received in slots 312 in a firing clip 310 that is attached to the proximal end 57 of compression shaft 56 by a protrusion 58 or other suitable fastener arrangements. Such arrangement permits the distal axial movement (arrow "DD") and the proximal axial movement (arrow "PD") of the compression shaft 56 by pivoting the trigger assembly 14 as will be further discussed below. The trigger assembly 14, the compression shaft portions 56, 65, 67 and the firing cap 310 and other related components may comprise a firing assembly generally designated as 320.

As can be seen in FIG. 3, the adjustment shaft 80 has a distal portion 81 that is attached to the top and bottom tension bands 65, 67 and a proximal portion 82 that is adjoined to the distal portion 81 by a reduced diameter segment 83. The proximal portion 82 is axially received within an axial passage 332 in the distal closure nut 330 that is keyed onto or otherwise attached to a proximal closure nut 340 to form a closure nut assembly generally designated as 342 such that the distal closure nut 330 and the proximal closure nut 340 may rotate together. See FIG. 4. The distal closure nut 330 may further have a distally extending hub portion 334 that abuts an inwardly extending retainer flange 335 formed inside the handle assembly 40. Such arrangement permits the distal closure nut 330 to freely rotate within the handle assembly 40, but is unable to move axially therewithin. Likewise, the proximal end portion 82 of the adjustment shaft 80 is axially received within an axial passage (not shown) within the proximal closure nut 340. Also in various embodiments, the closure knob assembly 350 is attached to the proximal end of the proximal closure nut 340. Rotation of the closure knob assembly 350 will cause the proximal closure nut 340 and distal closure nut 330 to also rotate. In various embodiments, the adjustment shaft 80 may be axially movably supported within a handle assembly 40 of the type and construction disclosed in U.S. Patent Publication No. US-2008-0078806-A1 to Todd Philip Omaits, et al., filed Sep. 29, 2006 that is owned by the Assignee of the present application and which is herein incorporated by reference in its entirety. However, other handle and firing system arrangements may be employed without departing from the spirit and scope of the present invention.

As can also be seen in FIG. 3, the handle assembly 40 may further include an anvil force measurement system 500 for providing the clinician with a means for monitoring the amount of clamping force being applied to the tissue. In one form, for example, the force measurement system 500 may comprise an indicator 502 that is viewable through the handle housing 41. The indicator 502 is attached to a proximal end 85 of the adjustment rod 80 to axially ride therewith. A compliant member, which may comprise a spring 504 or other member, is attached between the proximal end portion 85 of the adjustment rod 80 and a distal end portion 87 of the adjustment rod 80. When applying compression to the tissue, the compliant member 504 will then stretch depending upon the amount of force being applied. One then measures the relative displacement across the compliant member 504 to establish the force applied. The indicator 502 cooperates with a scale 505 that is calibrated to provide the clinician with a readout of the amount of clamping force being applied to the tissue. Other force measurement systems may also be employed. For example, load cells, strain gauges, etc. could also be incorporated to provide the clinician with an indication of the amount of force being applied to the tissue.

Various embodiments of the present invention include a unique and novel anvil locking system generally designated as 400 for, among other things, locking the anvil 100 in an axial position relative to the staple head assembly 12 during firing. One embodiment of the anvil locking system 400 includes a first locking member 402 that is coupled to the distal end portion 81 of the adjustment shaft 80. In various embodiments, the first locking member comprises an elongated gear rack 402. The gear rack 402 may be integrally formed with or otherwise attached to the distal end portion 81 of the adjustment shaft 80. Thus, the gear rack 402 will move axially with the adjustment shaft 80 in the proximal direction "PD" and the distal direction "DD".

Figure 5:
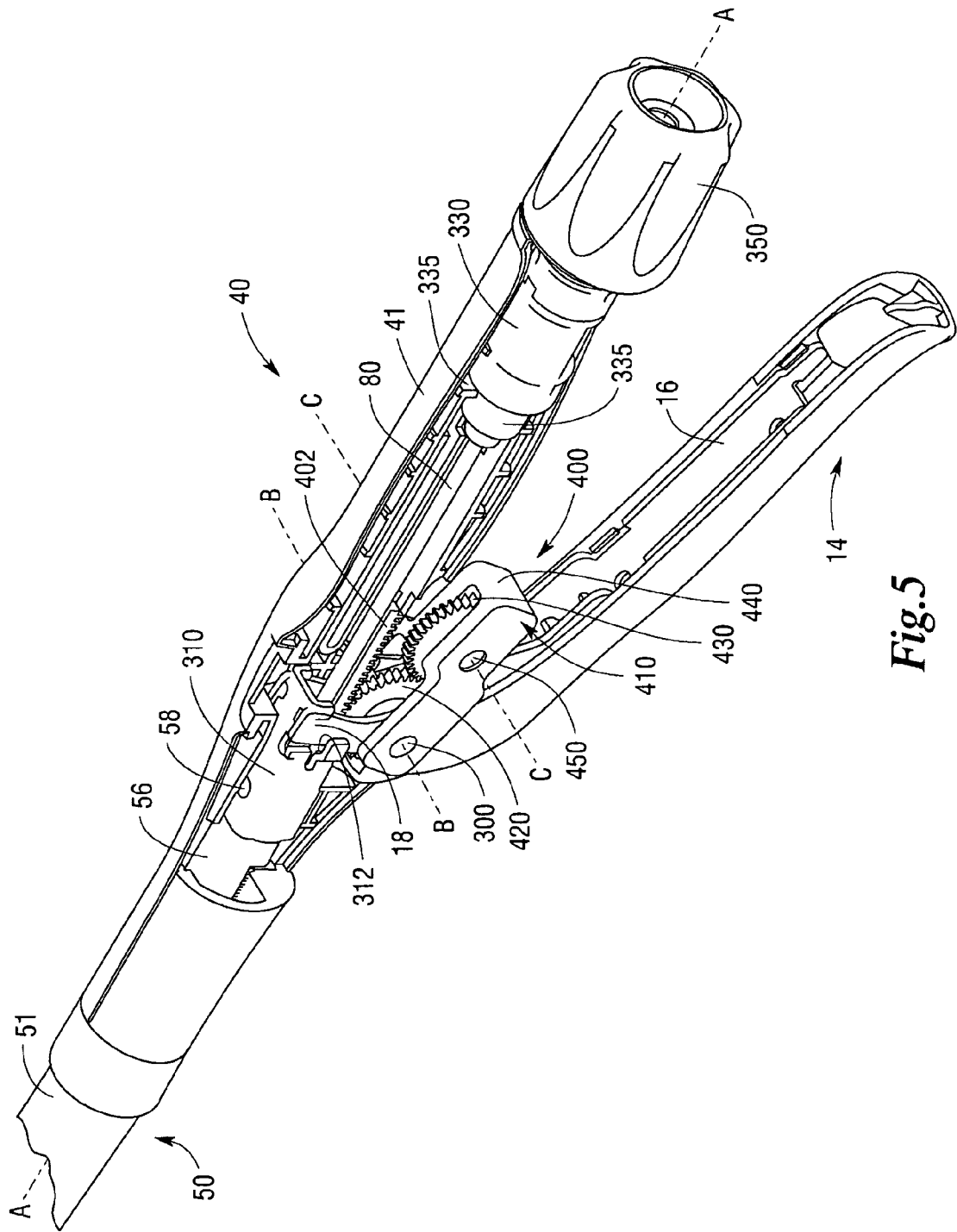
FIG. 5 is another perspective view of the surgical stapling instrument embodiment of FIGS. 1, 3, and 4 with a portion of the handle housing removed and the anvil locking system in an unlocked position.

As can be seen in FIGS. 3 and 4, the anvil locking system 400 may further include a locking assembly 410 that may be pivotally coupled to the handle assembly 40 for selective engagement with the gear rack 402. In various embodiments, for example, the locking assembly 410 may include a first locking gear 420 that is rotatably mounted to the handle assembly 420 in meshing engagement with the gear rack 402. In various embodiments, the first locking gear 420 may be rotatably journaled on the pin 300 that pivotally couples the trigger frame 16 to the handle assembly 40. Thus, the first locking gear 420 is free to rotate about the pin 300 about a second locking axis B-B that is substantially transverse to a longitudinal axis A-A of the stapler 10. See FIG. 5.

The locking assembly 400 further includes a second locking gear 430 that is rotatably pinned to a locking yoke 440 by a pin 450. The locking yoke 440 has a distal end 442 that may also be rotatably mounted on pin 30 such that the locking yoke 440 may pivot about the second axis B-B. The pin 450 defines a third axis C-C that is also substantially transverse to the longitudinal axis A-A and substantially parallel to the second axis B-B. See FIG. 5. Pin 450 retains the second locking gear 430 in meshing engagement with the first locking gear 420.

Once the anvil 100 has been coupled to the trocar 60, the axial position of the anvil 100 relative to the staple cartridge 24 may be adjusted by rotating the closure knob 350 relative to the handle assembly 40. For example, by rotating the closure knob 350 in one direction, the anvil 100 is axially advanced in the distal direction "DD" away from the staple cartridge 24 to increase the gap "G" therebetween. By rotating the closure knob 350 in a second direction (opposite to the first direction), the anvil 100 is axially drawn towards the staple cartridge 24 in the proximal direction "PD" to thereby decrease the gap "G". See FIG. 3. Once the clinician has axially positioned the anvil 100 in a desired position relative to the staple cartridge 24, the instrument may be fired. During the positioning of the anvil, the clinician may observe the amount of compression force being applied to the tissue by monitoring the force measurement system 500. Once the tissue has been placed under a desired amount of compression between the anvil 100 and the staple cartridge 24, the anvil locking system 400 may be engaged to retain the anvil 100 in the desired axial position.

Figure 6:
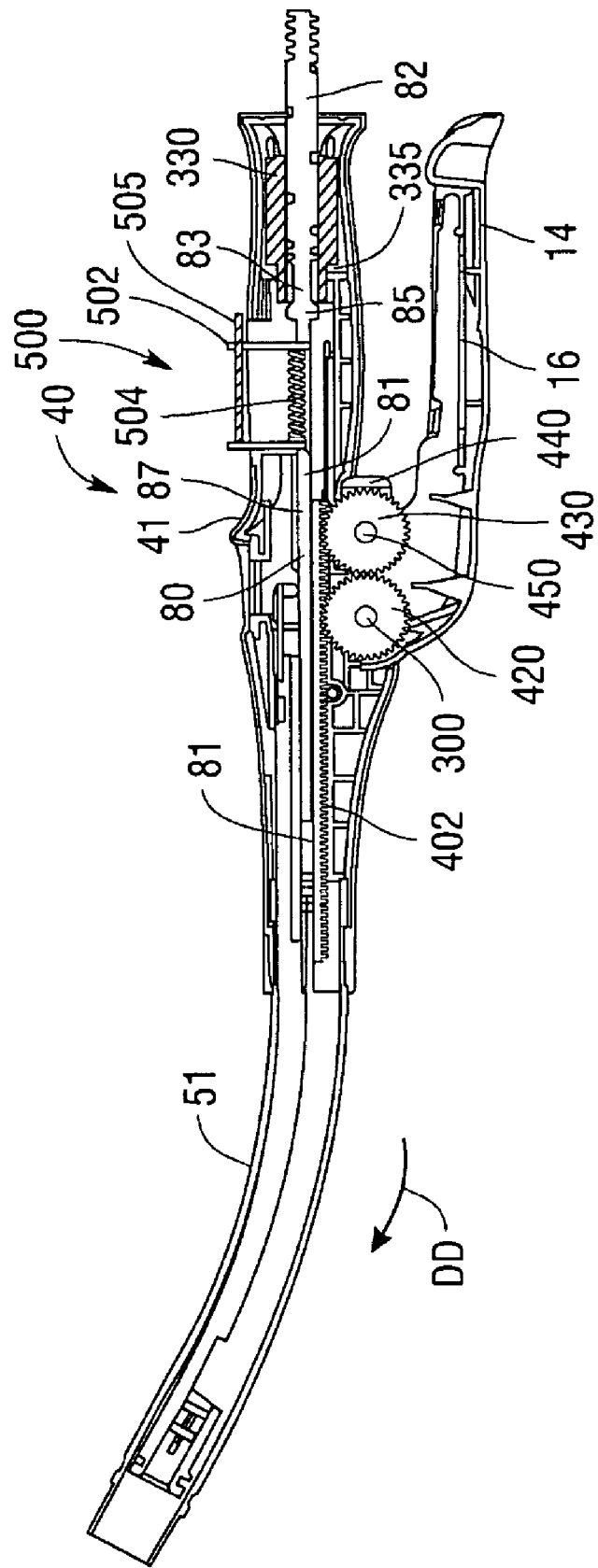
FIG. 6 is another partial cross-sectional view of a portion of the surgical stapling instrument embodiment of FIGS. 1 and 3-5 with the anvil locking system in a locked position.

As shown in FIG. 3, the anvil locking system 400 is in an unlocked position. When in the unlocked position, the second locking gear 430 is pivoted out of meshing engagement with the elongated gear rack 402 to thereby permit the gear rack 402 to move freely with the adjustment shaft 80 when axially positioning the anvil 100 relative to the staple cartridge 24. Once the anvil 100 has been positioned, the clinician simply pivots the locking yoke 440 about the second axis B-B to bring the second locking gear 430 into meshing engagement with the gear rack 402 as shown in FIG. 6. When the second locking gear 430 is in meshing engagement with the gear rack 402, further axial movement of the adjustment shaft 80 is prevented. Because the anvil 100 is attached to the trocar 60 which is attached to the adjustment shaft 80, further axial movement of the anvil 100 relative to the staple cartridge 24 is also prevented. The clinician retains the second locking gear 430 in meshing engagement with the gear rack 402 during firing of the instrument 10. If either gear 420, 430 tries to rotate as a result of gear rack 402 movement, it will be resisted by the opposite locking gear which will try to rotate in the opposite direction.

Those of ordinary skill in the art will appreciate that such arrangement serves to lock the anvil 100 in place prior and during firing of the staples. Because the first locking gear 420 is always in engagement with the gear rack 402 and the second locking gear 430 is engaged with the first locking gear 420, a locking engagement with the gear rack 402 can be achieved with high positional accuracy. A slight clearance may be provided between the locking yoke 440 and the pin 300 to allow for slight rack engagement errors without compromising positional accuracy. It will be further appreciated that the tooth profile on the gear rack 402 can also be advantageously designed to facilitate the arcuate motion of the second locking gear 430 during engagement.

Figure 7:
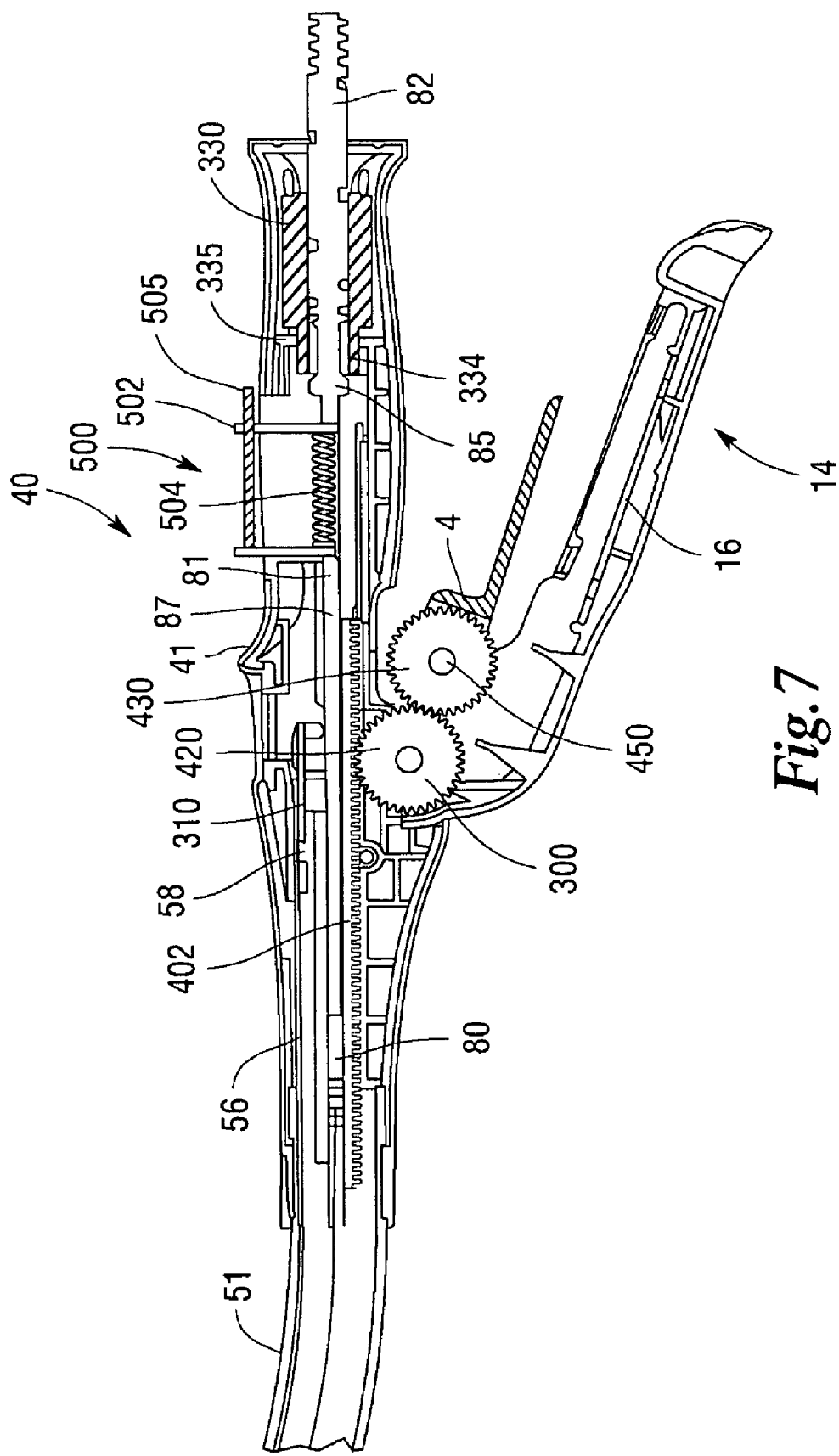
FIG. 7 is a partial cross-sectional view of a portion of another surgical stapling instrument embodiment of the present invention with the anvil locking system in an unlocked position.

In various embodiments, the locking yoke 440 may be provided in the configuration depicted in FIGS. 1-6. However, in alternative embodiments, the locking yoke 440' may be provided with an elongated actuation lever 441 (FIG. 7) which forms a lever arm to amplify the force applied to the pivot the second locking gear 430 into locking engagement with the locking rack 402. Such arrangement serves to establish sufficient normal force to maintain "three point engagement" between the gear rack 402 and the locking gears 420, 430 to prevent the second locking gear 430 from camming out of engagement with the locking rack 403 during firing of the instrument. Also in various embodiments, the locking yoke 440 may be configured to interact with the firing trigger assembly 14 such that pivoting of the firing trigger assembly 14 in the manner required to fire the staples will also pivot the locking yoke 440 sufficiently to cause the second locking gear 430 to mesh with the locking rack 402 in locking engagement therewith.

Figure 8:
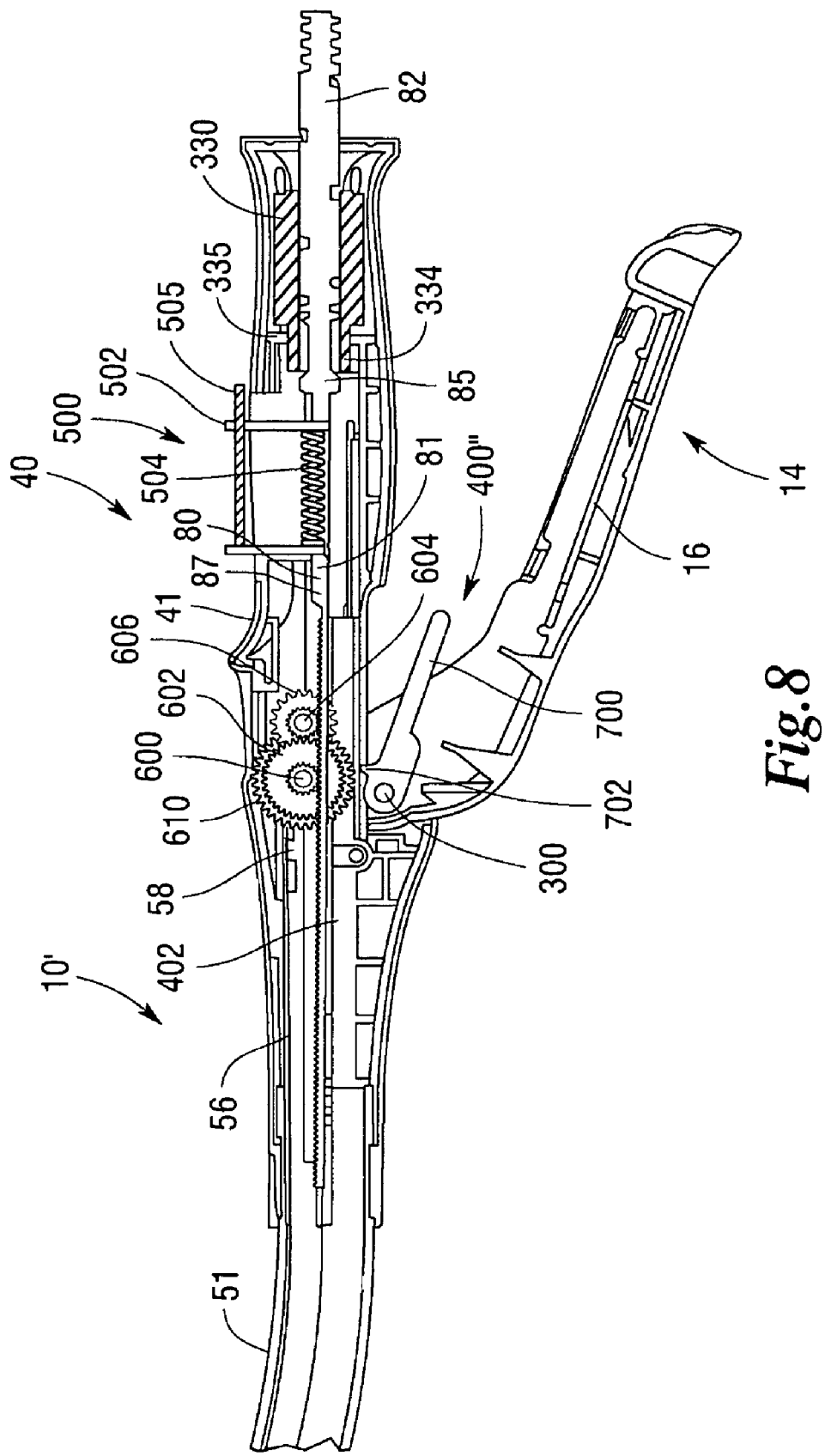
FIG. 8 is a partial cross-sectional view of a portion of another surgical stapling instrument embodiment of the present invention with the anvil locking system in an unlocked position.
Figure 9:
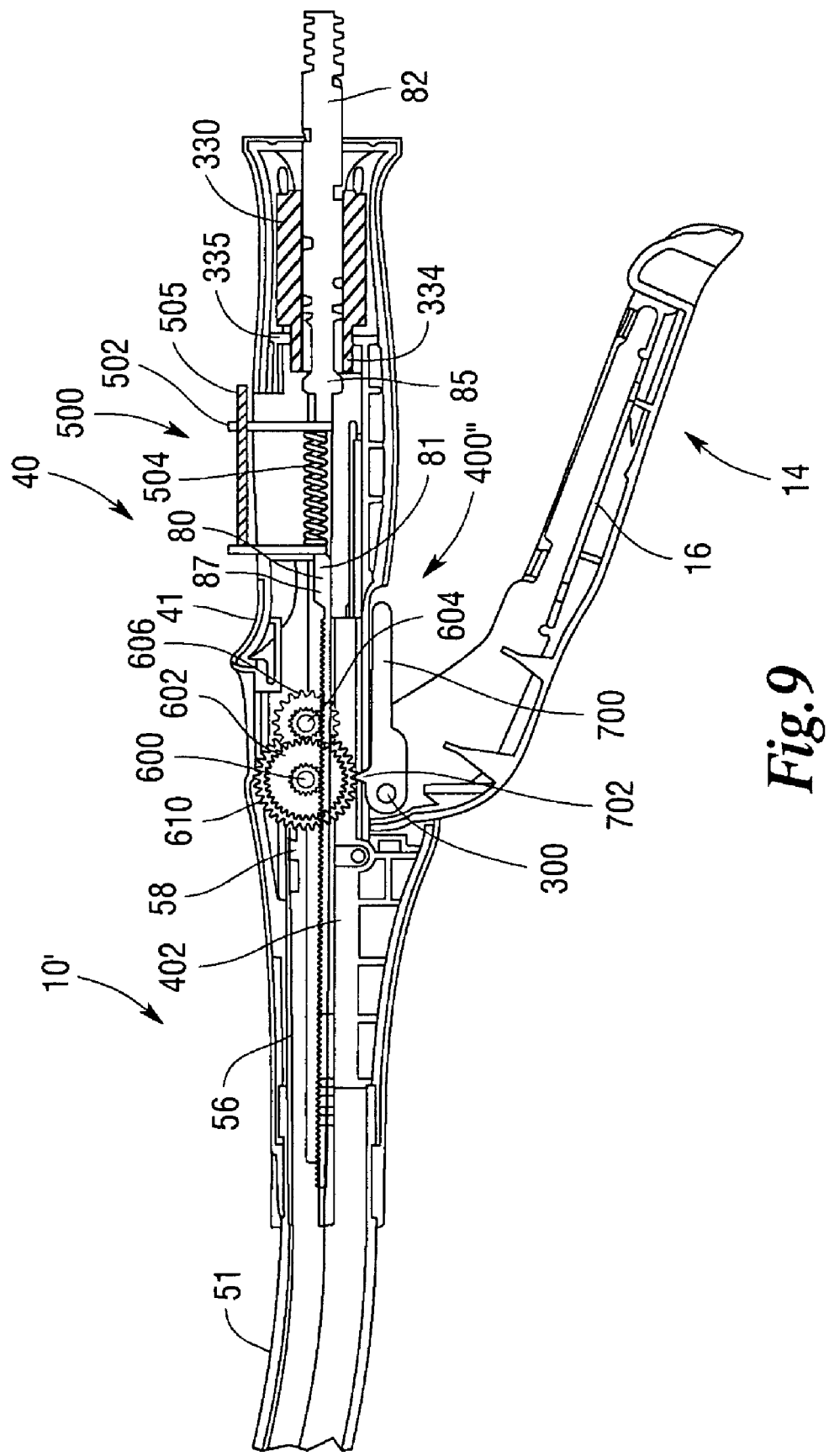
FIG. 9 is a partial cross-sectional view of a portion of the surgical stapling instrument embodiment of FIG. 8 with the anvil locking system in a locked position.
Figure 11:
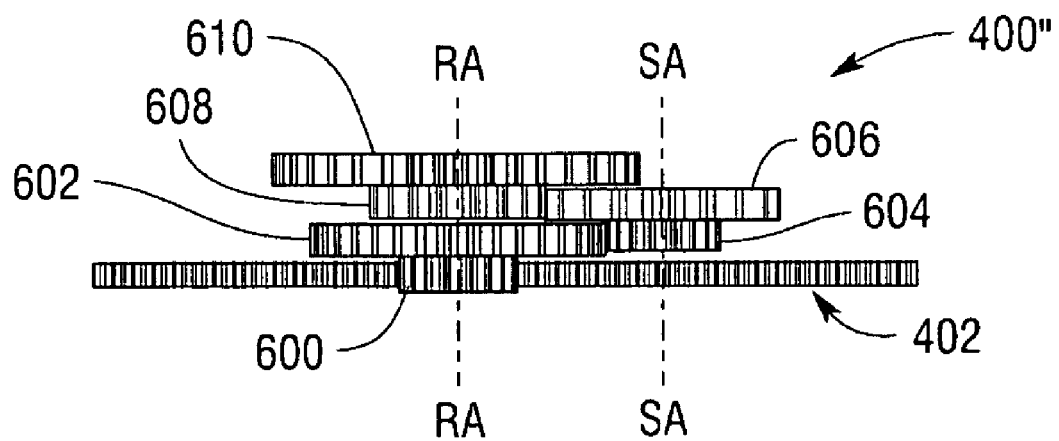
FIG. 11 is a top view of the gear assembly and gear rack embodiment of FIG. 10.
Figure 10:
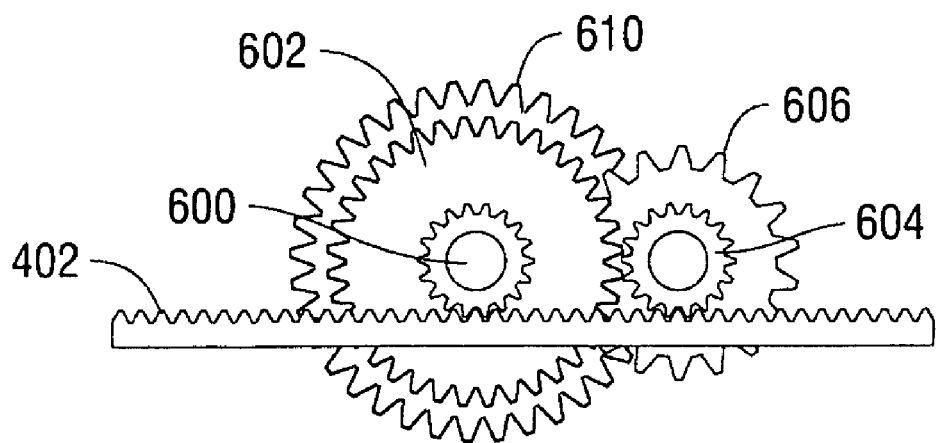
FIG. 10 is a partial side view of a gear assembly and gear rack embodiment of the anvil locking system depicted in FIGS. 8 and 9.

FIGS. 8 and 9 depict a portion of another circular stapler embodiment 10' of the present invention that is similar to the circular stapler 10 described above, except for the following differences. This embodiment employs a multi-gear locking system 400" for locking the anvil in position. As can be seen in FIGS. 8-11, the anvil locking system 400" includes a gear 600 that is in meshing engagement with the gear rack 402. As the gear rack 402 moves during the clamping process (in the manner described above), gear 600 turns. Gear 600 is attached to gear 602 which meshes with gear 604. Gear 604 is attached to gear 606 which meshes with gear 608. Gear 608 is attached to a locking gear 610. Gears 600, 608 and 610 are coaxially aligned along a rotational axis "RA-RA" as shown in FIG. 11. Gears 604, 606 are coaxially aligned on a second axis "SA-SA" that is substantially parallel to axis RA-RA. In various embodiments, at least one gear tooth 700 is provided on the trigger 14 as shown in FIGS. 8 and 9. To lock the gear rack 402 and thus the anvil in position, the clinician simply pivots a locking lever 700 that is pivotally coupled to the trigger 14 to bring a gear tooth 702 that is formed on the locking lever 700 into meshing engagement with the gear 610. See FIG. 9.

In various embodiments, the locking system 400" may be provided with the following gear ratios, for example:
Gear 600/602=⅓ gear ratio.
Gear 604/606=⅓ gear ratio.
Gear 608/610=¼ gear ratio.
Gear 600/610=1/36 ratio.
In various embodiments, gear 610 will turn approximately 36 times for every revolution of gear 600. Thus, the net result is that gear 610 can lock gear 600 using $1/36^{th}$ the amount of force, and for every tooth movement of gear 610, gear 600 will move $1/36^{th}$ of a tooth. Such advantage is a 36 to 1 increase in resolution at $1/36^{th}$ the force needed to lock the system. Other gear arrangements may also be successfully employed, however, without departing from the spirit and scope of the present invention.

When performing an anastomosis using a circular stapler, the intestine may be stapled using a conventional surgical stapler with multiple rows of staples being emplaced on either side of a target section (i.e., specimen) of intestine. The target section is typically simultaneously cut as the section is stapled. After removing the target specimen, the surgeon inserts the anvil into the proximal portion of the intestine, proximal of the staple line. This is typically done by inserting the anvil head into an entry port cut into the proximal intestine portion and forcing the anvil shaft through the proximal staple line. The instrument minus the anvil is passed transanally to the distal staple line and the anvil trocar is forced through the staple line. Next, the surgeon attaches the anvil to the trocar tip of the stapler. Once the anvil has been properly coupled to the trocar tip, the anvil is inserted into the distal portion of the intestine. The surgeon then begins to rotate the closure knob assembly 350 to draw the anvil 100 toward the cartridge 24 supported in the stapling head 12 to close the gap between the anvil 100 and cartridge 24 and thereby engage the proximal end of the distal intestine portion with the distal end of the proximal intestine portion in the gap. The surgeon continues to rotate the closure knob 350 until the desired gap G and tissue compression is attained. Thereafter, the surgeon may engage the anvil locking systems 400, 400', whichever the case may be and then fire the stapler 10 by depressing the firing trigger 14. Depressing the trigger 14 causes the compression shaft 56 to drive the staple driver 22 distally to drive the staples 90 to be driven through both ends of the intestine. Simultaneously, as the staples are driven and formed, the knife 70 is driven through the intestinal tissue ends, cutting the ends adjacent to the inner row of staples 90.

The various embodiments of the present invention represent a vast improvement over prior circular staple arrangements that fail to provide any means for locking the anvil in a firing position. While several embodiments of the invention have been described, it should be apparent, however, that various modifications, alterations and adaptations to those embodiments may occur to persons skilled in the art with the attainment of some or all of the advantages of the invention. For example, according to various embodiments, a single component may be replaced by multiple components, and multiple components may be replaced by a single component, to perform a given function or functions. This application is therefore intended to cover all such modifications, alterations and adaptations without departing from the scope and spirit of the disclosed invention as defined by the appended claims.

The devices disclosed herein can be designed to be disposed of after a single use, or they can be designed to be used multiple times. In either case, however, the device can be reconditioned for reuse after at least one use. Reconditioning can include an combination of the steps of disassembly of the device, followed by cleaning or replacement of particular pieces, and subsequent reassembly. In particular, the device can be disassembled, and any number of particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those of ordinary skill in the art will appreciate that the reconditioning of a device can utilize a variety of different techniques for disassembly, cleaning/replacement, and reassembly. Use of such techniques, and the resulting reconditioned device, are all within the scope of the present application.

Preferably, the invention described herein will be processed before surgery. First a new or used instrument is obtained and, if necessary, cleaned. The instrument can then be sterilized. In one sterilization technique, the instrument is placed in a closed and sealed container, such as a plastic or TYVEK® bag. The container and instrument are then placed in a field of radiation that can penetrate the container, such as gamma radiation, x-rays, or higher energy electrons. The radiation kills bacteria on the instrument and in the container. The sterilized instrument can then be stored in the sterile container. The sealed container keeps the instrument sterile until it is opened in the medical facility.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

The invention which is intended to be protected is not to be construed as limited to the particular embodiments disclosed. The embodiments are therefore to be regarded as illustrative rather than restrictive. Variations and changes may be made by others without departing from the spirit of the present invention. Accordingly, it is expressly intended that all such equivalents, variations and changes which fall within the spirit and scope of the present invention as defined in the claims be embraced thereby.

What is claimed is:

1. A surgical stapling instrument, comprising:
   a handle assembly;
   a shaft assembly coupled to said handle assembly;
   a stapling head assembly operably coupled to said shaft assembly, said stapling head assembly comprising:
      a staple cartridge for supporting one or more surgical staples;
      a staple driver for engaging and driving the staples from said staple cartridge; and
      a knife movably supported in said stapling head assembly;
   a drive system for applying drive motions to said staple driver and said knife;
   an anvil movably supported relative to said staple cartridge for axial movement toward and away from said staple cartridge;
   an anvil adjustment assembly for selectively adjusting an axial position of the anvil relative to the staple cartridge, said anvil adjustment assembly comprising:
      an adjustment shaft movably supported by said handle assembly for selective axial travel therethrough; and
      a trocar portion coupled to said adjustment shaft for axial travel therewith, said trocar portion configured for removable attachment to said anvil and wherein said surgical stapling instrument further comprises:
   a force measurement system operably interfacing with said anvil adjustment assembly for measuring an amount of compression force applied to tissue clamped between said anvil and said staple cartridge; and
   an anvil locking system configured to cooperate with said anvil adjustment assembly to selectively lock and unlock the anvil in axial position relative to said staple cartridge, said anvil locking system comprising:
      an elongated gear rack coupled to one of said adjustment shaft and said trocar portion; and
      a locking assembly pivotally coupled to said handle assembly and configured to pivot between positions wherein said lockinq assembly retainingly engages said elongated gear rack and a position wherein said locking assembly does not engage said elongated gear rack.

2. The surgical stapling instrument of claim 1 wherein said locking assembly comprises:
   a first locking gear in meshing engagement with said elongated gear rack; and a second locking gear movably supported relative to said elongated gear rack for selectively meshing engagement therewith while being in meshing engagement with said first locking gear.

3. The surgical stapling instrument of claim 2 wherein said first and second locking gears are operably supported in a locking yoke pivotally supported relative to said handle assembly.

4. The surgical stapling instrument of claim 3, wherein said locking yoke has a actuation lever protruding therefrom.

5. A circular surgical stapling instrument, comprising:
a handle assembly;
a stapling head assembly operably coupled to said handle assembly;
an anvil movably supported relative to said stapling head assembly for selective axial travel toward and away from said stapling head assembly;
an anvil adjustment assembly supported by said handle assembly for selectively adjusting an axial position of the anvil relative to the staple cartridge, said anvil adjustment assembly comprising:
an adjustment shaft movably supported by said handle assembly for selective axial travel therethrough; and
a trocar portion coupled to said adjustment shaft for axial travel therewith, said trocar portion configured for removable attachment to said anvil, and wherein said circular surgical stapling instrument further comprises:
a force measurement system operably interfacing with said anvil adjustment assembly for measuring an amount of compression force applied to tissue clamped between said anvil and said stapling head; and
an anvil locking system configured to cooperate with said anvil adjustment assembly to selectively lock and unlock the anvil in axial positions relative to said stapling head, said anvil locking system comprising:
an elongated gear rack coupled to one of said adjustment shaft and said trocar portion; and
a locking assembly pivotally coupled to said handle assembly and configured to pivot between positions wherein said locking assembly retainingly engages said elongated gear rack and a position wherein said locking assembly does not engage said elongated gear rack.

6. The surgical stapling instrument of claim 5 wherein said locking assembly comprises:
a first locking gear in meshing engagement with said elongated gear rack; and
a second locking gear movably supported relative to said elongated gear rack for selectively meshing engagement therewith while being in meshing engagement with said first locking gear.

7. The surgical stapling instrument of claim 6 wherein said first and second locking gears are operably supported in a locking yoke pivotally supported relative to said handle assembly.

8. The surgical stapling instrument of claim 7, wherein said locking yoke has a actuation lever protruding therefrom.

9. A surgical stapling instrument, comprising:
a handle assembly;
a shaft assembly coupled to said handle assembly;
a stapling head assembly operably coupled to said shaft assembly, said stapling head assembly comprising:
a staple cartridge for supporting one or more surgical staples;
a staple driver for engaging and driving the staples from said staple cartridge; and
a knife movably supported in said stapling head assembly;
a drive system for applying drive motions to said staple driver and said knife;
an anvil movably supported relative to said staple cartridge for axial movement toward and away from said staple cartridge;
an anvil adjustment assembly for selectively adjusting an axial position of the anvil relative to the staple cartridge, said anvil adjustment assembly comprising:
an adjustment shaft movably supported by said handle assembly for selective axial travel therethrough; and
a trocar portion coupled to said adjustment shaft for axial travel therewith, said trocar portion configured for removable attachment to said anvil and wherein said surgical stapling instrument further comprises:
a force measurement system operably interfacing with said anvil adjustment assembly for measuring an amount of compression force applied to tissue clamped between said anvil and said staple cartridge; and
an anvil locking system configured to cooperate with said anvil adjustment assembly to selectively lock and unlock the anvil in axial position relative to said staple cartridge, said anvil locking system comprising:
an elongated gear rack; and
a gear assembly in meshing engagement with said elongated gear rack and further oriented for selective engagement with a second locking member pivotally coupled to said handle assembly and configured to pivot between positions wherein said second locking member retainingly engages said elongated gear rack and a position wherein said second locking member does not engage said elongated gear rack.

10. The surgical stapling instrument of claim 9 wherein said gear assembly comprises:
a first gear in meshing engagement with said elongated gear rack;
a second gear coupled to said first gear;
a third gear in meshing engagement with said elongated gear rack and said second gear;
a fourth gear coupled to said third gear;
a fifth gear in meshing engagement with said fourth gear; and
a sixth gear coupled to said fifth gear and oriented for selective meshing engagement with said second locking member.

11. The surgical stapling instrument of claim 10 wherein said second locking member comprises:
a locking lever pivotally supported on said handle assembly; and
at least one locking tooth formed on said locking lever.

12. A circular surgical stapling instrument, comprising:
a handle assembly;
a stapling head assembly operably coupled to said handle assembly;
an anvil movably supported relative to said stapling head assembly for selective axial travel toward and away from said stapling head assembly;
an anvil adjustment assembly supported by said handle assembly for selectively adjusting an axial position of the anvil relative to the staple cartridge, said anvil adjustment assembly comprising:
an adjustment shaft movably supported by said handle assembly for selective axial travel therethrough; and
a trocar portion coupled to said adjustment shaft for axial travel therewith, said trocar portion configured for removable attachment to said anvil, and wherein said circular surgical stapling instrument further comprises:

a force measurement system operably interfacing with said anvil adjustment assembly for measuring an amount of compression force applied to tissue clamped between said anvil and said stapling head; and an anvil locking system configured to cooperate with said anvil adjustment assembly to selectively lock and unlock the anvil in axial positions relative to said stapling head, said anvil locking system comprising:
an elongated gear rack; and
a gear assembly in meshing engagement with said elongated gear rack and selective engagement with a locking assembly pivotally coupled to said handle assembly and configured to pivot between positions wherein said locking assembly retainingly engages said elongated gear rack and a position wherein said locking assembly does not engage said elongated gear rack.

13. The surgical stapling instrument of claim 12 wherein said gear assembly comprises:
a first gear in meshing engagement with said elongated gear rack;
a second gear coupled to said first gear;
a third gear in meshing engagement with said elongated gear rack and said second gear;
a fourth gear coupled to said third gear;
a fifth gear in meshing engagement with said fourth gear; and
a sixth gear coupled to said fifth gear and oriented for selective meshing engagement with said second locking member.

14. A surgical circular stapling instrument, comprising:
a stapling head assembly;
an anvil movably supported relative to said stapling head assembly for axial movement toward and away from said stapling head by an adjustment shaft interfacing with said anvil;
a force measurement system operably interfacing with said anvil and said adjustment shaft for measuring an amount of compression force applied to tissue clamped between said anvil and said stapling head assembly;
an elongated gear rack coupled to said adjustment shaft; and
a locking assembly configured to move between positions wherein said locking assembly retainingly engages said elongated gear rack to prevent further axial movement of said adjustment shaft and a position wherein said locking assembly does not engage said elongated gear rack to allow axial movement of said adjustment shaft.

* * * * *